United States Patent
Casalini

(10) Patent No.: US 12,337,225 B2
(45) Date of Patent: Jun. 24, 2025

(54) METHOD FOR CONTROLLING A CONTROL INTERFACE OF AN EXERCISE MACHINE DURING THE CONSUMPTION OF MULTIMEDIA CONTENT AND RELATED MACHINE

(71) Applicant: TECHNOGYM S.P.A., Cesena (IT)

(72) Inventor: Filippo Casalini, Cesena (IT)

(73) Assignee: TECHNOGYM S.P.A., Cesena (IT)

( * ) Notice: Subject to any disclaimer, the term of this patent is extended or adjusted under 35 U.S.C. 154(b) by 394 days.

(21) Appl. No.: 17/342,287

(22) Filed: Jun. 8, 2021

(65) Prior Publication Data
US 2021/0387073 A1 Dec. 16, 2021

(30) Foreign Application Priority Data
Jun. 12, 2020 (IT) ........................ 102020000014092

(51) Int. Cl.
*A63B 71/06* (2006.01)
*A63B 24/00* (2006.01)

(52) U.S. Cl.
CPC ...... *A63B 71/0622* (2013.01); *A63B 24/0087* (2013.01); *A63B 2024/009* (2013.01); *A63B 2071/063* (2013.01); *A63B 2071/065* (2013.01); *A63B 2071/0675* (2013.01); *A63B 2220/62* (2013.01)

(58) Field of Classification Search
CPC ........ A63B 71/0622; A63B 2071/0675; A63B 2220/62; A63B 24/0075; A63B 2071/065; A63B 2024/0078; A63B 2024/009; A63B 2071/0641; A63B 24/0087; A63B 2071/063; A63B 71/0054; A63B 2021/009
See application file for complete search history.

(56) References Cited

U.S. PATENT DOCUMENTS

| | | | | |
|---|---|---|---|---|
| 9,367,668 B2* | 6/2016 | Flynt | ................ | A63B 71/0622 |
| 2013/0225370 A1 | 8/2013 | Flynt | | |
| 2014/0194248 A1* | 7/2014 | Kolman | ............ | A63B 71/0622 482/4 |
| 2015/0181314 A1* | 6/2015 | Swanson | ................ | G01S 19/19 340/870.07 |
| 2016/0256745 A1* | 9/2016 | Brammer | ............... | A63B 22/04 |
| 2019/0111318 A1* | 4/2019 | Evancha | ............ | A63B 24/0087 |
| 2019/0336827 A1* | 11/2019 | Intonato | ............ | A63B 71/0622 |

OTHER PUBLICATIONS

Extended European Search Report for 21178596.9 dated Nov. 4, 2021.
Search Report for IT 2020000014092 dated Feb. 26, 2021.

* cited by examiner

*Primary Examiner* — Megan Anderson
(74) *Attorney, Agent, or Firm* — Ferguson Case Orr Paterson

(57) ABSTRACT

A method including: providing multimedia content of a personal trainer preparatory to performing a set workout program on an exercise machine, usable through a control interface; associating configuration instructions of the exercise machine with the multimedia content, synchronized with playing of the multimedia content; during the enjoyment of the multimedia content, if a playing time instant falls within a set time interval provided by the configuration instructions, dynamically modifying the control interface so that the exercise machine assumes a respective operating configuration corresponding to the set time interval and showing the user on a display module, temporary controls usable through the control interface; and setting the exercise machine accordingly.

17 Claims, 11 Drawing Sheets

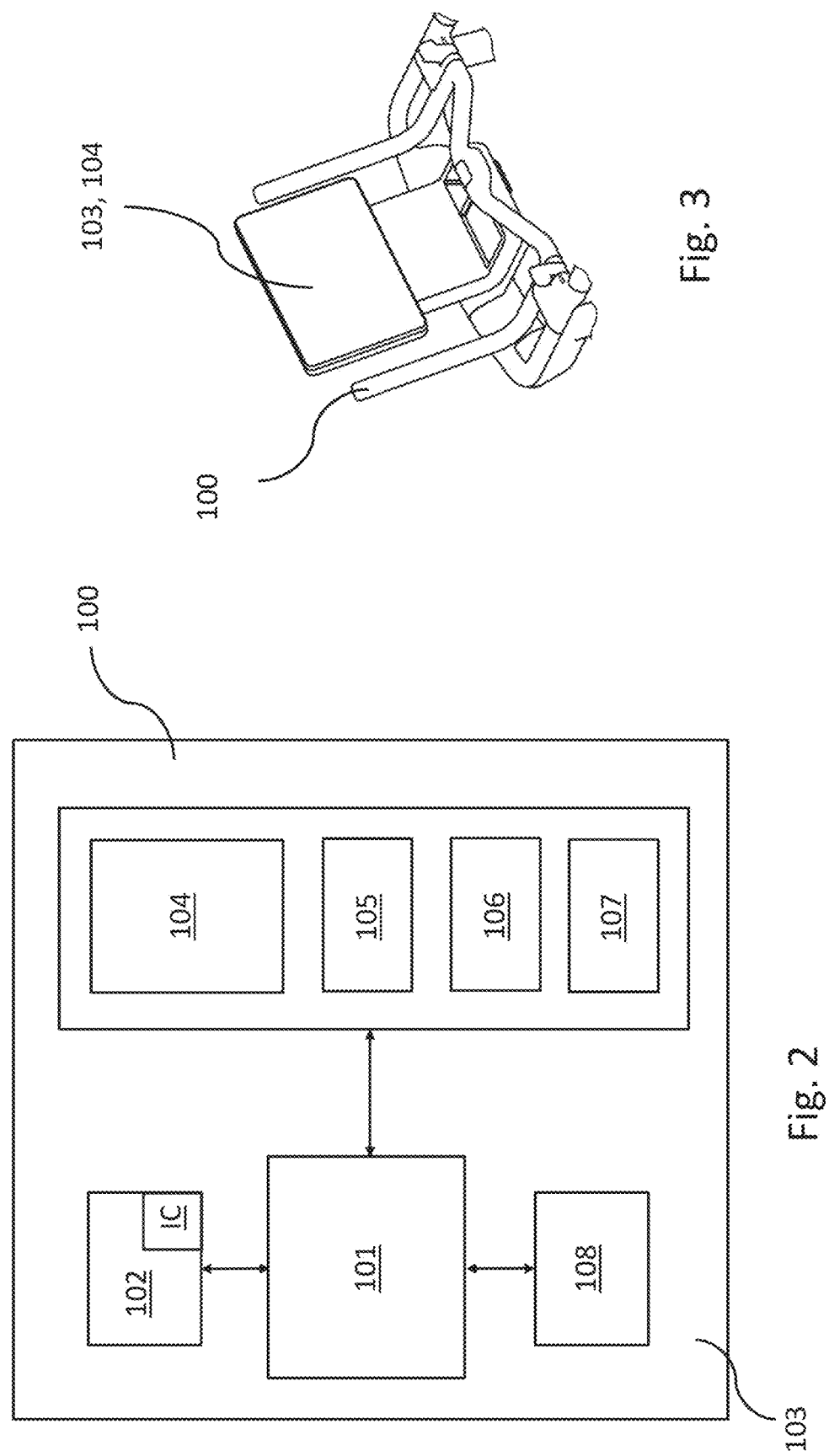

METHOD FOR CONTROLLING A CONTROL INTERFACE OF AN EXERCISE MACHINE DURING THE CONSUMPTION OF MULTIMEDIA CONTENT AND RELATED MACHINE

CROSS REFERENCE TO RELATED APPLICATION

This application claims priority to and benefit of Italian Patent Application No. 102020000014092, filed on Jun. 12, 2020, which is fully incorporated by reference herein in its entirety.

FIELD OF THE INVENTION

The present invention relates to the fitness sector, and in particular to a method for controlling a control interface of an exercise machine during the enjoyment of multimedia content, as well as to a related exercise machine.

BACKGROUND OF THE INVENTION

Nowadays, a user can enjoy multimedia content while working out on an exercise machine.

The multimedia contents may be simple entertainment or preparatory to the workout, such as a film of a personal trainer providing the user with voice messages to perform the workout according to a set workout program and other motivational messages and/or advice to help the user improve workout performance.

In greater detail, to perform the workout according to a set workout program, the personal trainer may ask the user to vary the setting of the exercise machine for a set time interval.

For example, if the exercise machine is a treadmill, the personal trainer may suggest slope and speed values to the user of the treadmill to be maintained for a set warm-up time interval and, subsequently, suggest slope and speed values of the treadmill to be maintained for a set workout time interval.

The setting of the exercise machine is the responsibility of the user, who, after receiving suggestions from the personal trainer, operates the respective controls on the control interface of the exercise machine.

This mode of operation is not free from flaws.

First of all, during the effort, the user may not have the necessary lucidity to promptly locate the controls on the control interface to vary the setting of the exercise machine with the risk of not being able to correctly perform the workout as per the set workout program.

Also, the presence of other sounds, such as background music or noise within the workout environment in general, especially if frequented by other users, can make it difficult for the user to perceive voice prompts provided by the personal trainer.

Furthermore, a control interface typically has a plurality of controls so there is a high risk of error by the user who, by pressing the wrong button, in addition to not being able to perform the workout properly as per the set workout program, could also be subject to additional and unexpected efforts with the risk of injury or falls.

This is even more apparent in a touchscreen control interface in which controls are touch-sensitive and the probability of accidental pressure by an inexperienced user increases considerably.

The aforesaid drawbacks are even more pronounced if the control interface is also provided with a display through which the user can enjoy the multimedia content of the personal trainer.

Indeed, in this case, it is increasingly difficult for the user to identify and operate the correct controls as the user tends to concentrate on the multimedia content.

Therefore, nowadays a need is strongly felt to have an exercise machine the control interface of which has a setting mode, during the enjoy of a multimedia content by a user in a workout, which is as user-friendly, simple and timely as possible and such as to ensure a reliable safety level.

SUMMARY OF THE INVENTION

It is an object of the present invention to provide a method of controlling a control interface of an exercise machine during the enjoy of a multimedia content which makes it possible to at least partially avoid the drawbacks of the prior art, and, in particular, which allows setting the exercise machine in a user-friendly, simple and timely manner, ensuring a reliable level of safety.

Such an object is achieved by a method as described and claimed herein.

Preferred embodiments are also described.

It is a further object of the present invention an exercise machine implementing such a method.

BRIEF DESCRIPTION OF THE FIGURES

Further features and advantages of the method and exercise machine according to the present invention will be apparent from the following description which illustrates preferred embodiments, given by way of indicative, non-limiting examples, with reference to the accompanying figures, in which:

FIG. 2 illustrates, by means of a block chart, an exercise machine according to an embodiment of the present invention;

FIG. 3 illustrates an enlargement of the exercise machine in FIG. 1a;

It is worth noting that equivalent or similar elements are indicated by the same numerical and/or alphanumerical reference in the figures.

DETAILED DESCRIPTION

An exercise machine 100 which can be used by a user to perform a physical activity, according to the present invention, will now be described with reference to the figures.

The exercise machine 100 may be any exercise machine employable by a user to perform physical activity remotely (e.g., from home), either alone or in a workout class, or to perform physical activity in a gym, either alone or in a workout class.

Examples of exercise machines 100 are a treadmill (FIGS. 1a and 3), a bike or exercise bike (FIG. 1b), a rowing machine, an indoor cycling machine, a strength exercise machine (FIGS. 1c and 1d), a station for practicing boxing (FIG. 1e), and so on.

Figure 1B:
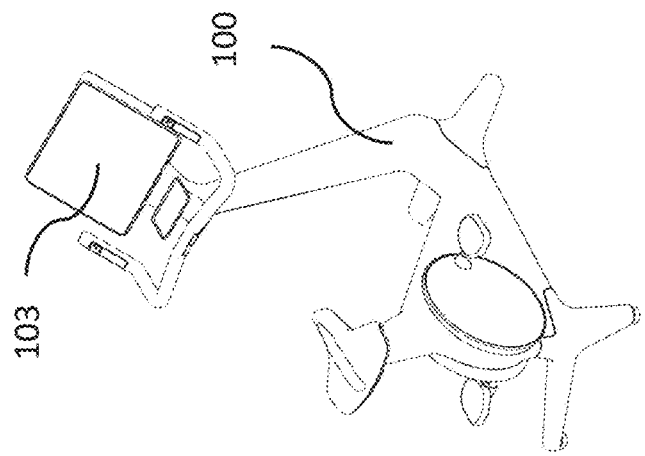
FIGS. 1a, 1b, 1c, 1d and 1e illustrate examples of an exercise machine usable by a user to perform a physical activity.
Figure 1A:
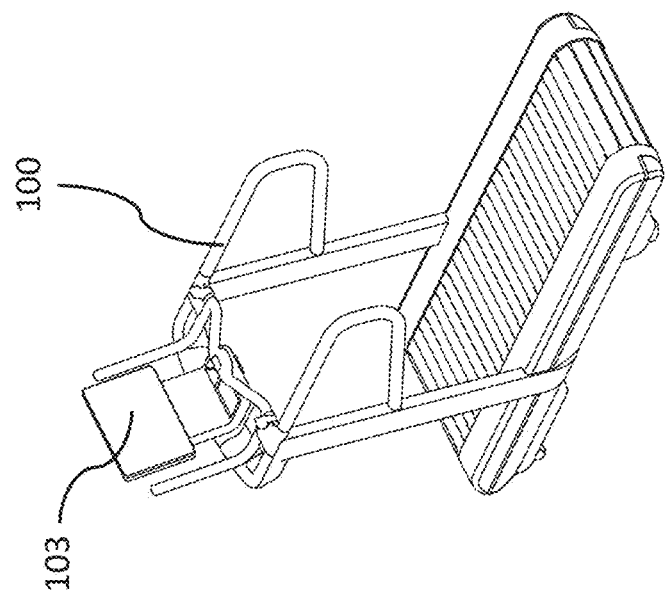
Figure 1D:
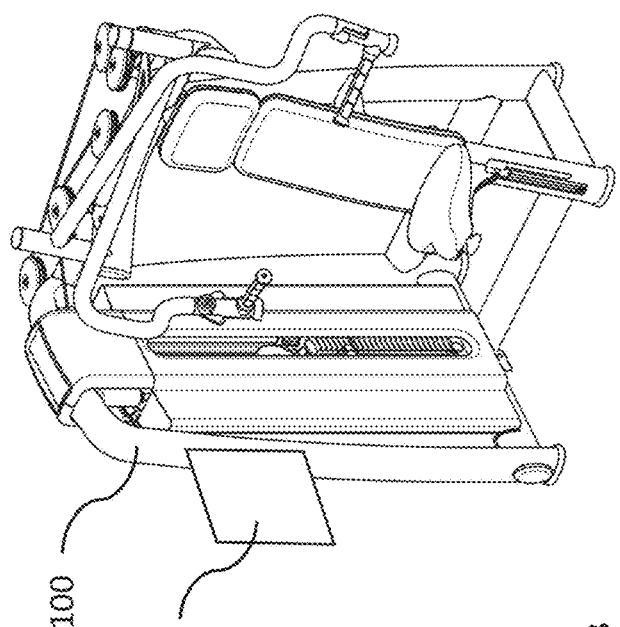
Figure 1E:
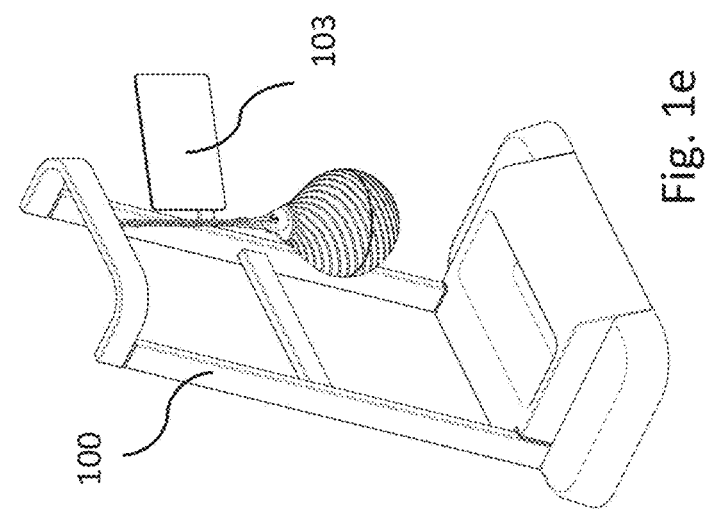
Figure 1C:
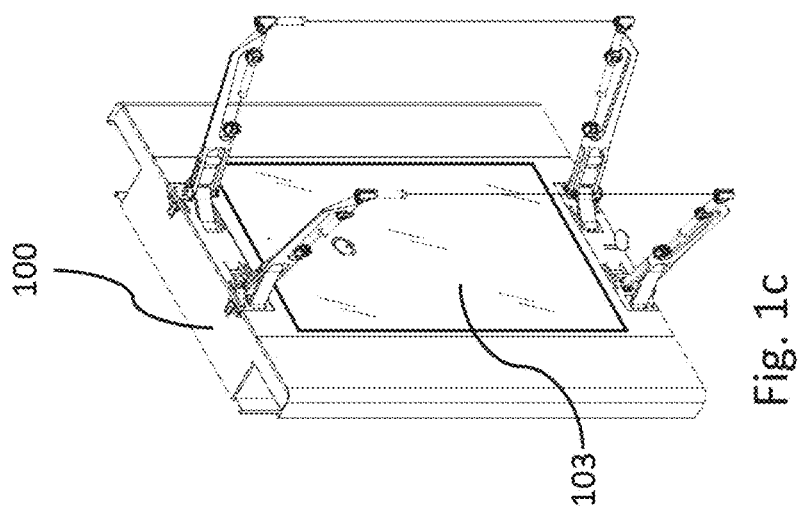

The following description, with particular reference to FIG. 2, applies to any of the exercise machines 100 shown in FIGS. 1a, 1b and 1c.

The exercise machine 100 comprises a data processing unit 101, e.g., a microprocessor or a microcontroller.

The exercise machine 100 further comprises a local memory unit 102, operatively connected to the data processing unit 101.

The local memory unit 102 can be either internal or external (e.g., as shown in FIG. 2) to the data processing unit 101.

It is worth noting that the local memory unit 102 is configured to store one or more program codes which can be executed by the data processing unit 101 and data generated and processed following the execution of one or more program codes.

The data processing unit 101 is configured to control the operation of the exercise machine 100.

Furthermore, the data processing unit 101 is configured to execute a method for controlling a control interface of an exercise machine during the enjoy of a multimedia content as described hereinafter.

The multimedia content, described in greater detail below, is indicated in the figures by the alphanumeric reference CM.

It is worth noting that the functions of the exercise machine 100, in particular for implementing such a method, will be described below.

Turning back to FIG. 2, the exercise machine 100 further comprises a control interface 103, operatively connected to the data processing unit 101, configured to allow a user to interact with the exercise machine 100.

The control interface 103 is configured to allow the user to be able to enjoy multimedia content while performing physical activity.

The multimedia content may be for entertainment purposes only (e.g., Internet browsing, entertainment videos, audio/video music files, etc.), or for workout purposes, e.g., audio messages and/or video which explain how to use the exercise machine and/or perform the workout on the exercise machine according to a set workout program to the user.

For the purposes of the present invention, reference will be made to the multimedia content of a personal trainer preparatory to performing a set workout program on the exercise machine, which can be enjoyed by a user through the control interface 103 of the exercise machine 100.

In this regard, the multimedia content can be an audio and/or video of a personal trainer who provides the user with voice and/or gestural messages to perform the workout according to a set workout program (e.g., how to change the setting of the exercise machine) and other motivational messages and/or useful tips that help the user to perform the workout correctly and improve performance.

Such previously recorded multimedia content (audio and/or video of the personal trainer) is loaded into the memory unit 102 of the exercise machine 100 and is made available on-demand by the data processing unit 101 of the exercise machine 100 at the user's request.

Figure 4A:
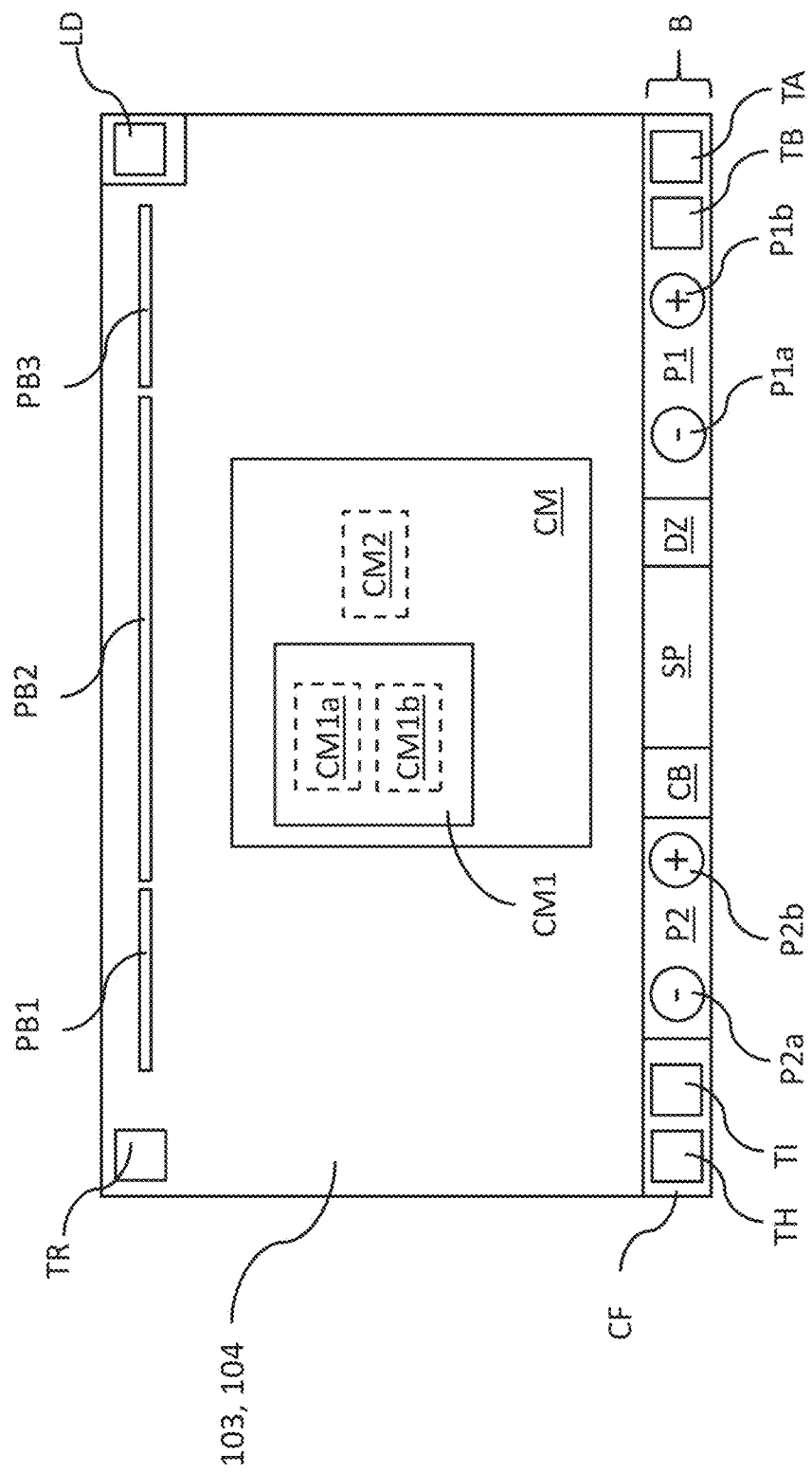
FIG. 4a diagrammatically illustrates a screen of a control interface of an exercise machine which shows components displayable in an operating configuration, according to an embodiment.

In an embodiment, diagrammatically shown in FIG. 4a, the multimedia content CM (audio and/or video of the personal trainer) comprises at least one audio component CM1.

According to a further embodiment, in combination with the preceding one, the multimedia content CM preferably comprises at least one video component CM2, in combination with the at least one audio component CM1.

It is worth noting that the at least one audio component CM1 and the at least one video component CM2 are mutually synchronized.

In an embodiment, the at least one audio component CM1 comprises only the personal trainer's voice.

According to a further embodiment, the at least one audio component CM1 may comprise a first audio sub-component CM1a representing the personal trainer's voice and a second audio sub-component CM1b representing background music (instrumental only or also with a voice part).

Turning back to FIG. 2, according to an embodiment, in combination with any one of those described above, the control interface 103 is of the touchscreen type.

The control interface 103 further comprises a display module (display) 104.

The display module 104 is employable by the user to interact with the control interface 103 during use of the exercise machine 100 for performing physical activity.

In greater detail, the display module 104 is configured to show multimedia content, defined and described above, to the user also including multimedia content of a personal trainer (audio and/or video) preparatory to the performance of the user's physical activity on the exercise machine 100.

In a preferred embodiment, in which the control interface 103 is of the touchscreen type, the display module 104 coincides with the control interface 103.

In this regard, it is worth noting that the multimedia content CM, diagrammatically shown as a rectangle in FIG. 4a, at the central position which would be occupied by the personal trainer, may be extended to the entire size of the display module 104, i.e., for example, with the personal trainer in the center of the display module 104 and moving images, such as a landscape or fantasy motifs, in the background.

According to an embodiment, the display module 104 is further configured to provide the user with content representative of use of the exercise machine 100, such as initial menu screen for setting the workout, workout parameters updated during the workout, workout summary screen, and so forth, and a plurality of controls made available to the user, before and during the workout, for interacting with and setting the exercise machine 100.

As diagrammatically shown in FIG. 4a, the plurality of controls, according to an embodiment, comprises fixed controls CF, i.e., controls which are displayed at fixed portions in time of the display module 104 of the control interface 103.

Furthermore, according to an embodiment, in combination with the preceding one, the plurality of controls comprises temporary controls CV, i.e., controls which are displayed for set time intervals in respective portions, preferably either different from or partially superimposing the fixed portions intended for the fixed controls CF, of the display module 104 of the control interface 103.

Examples of said plurality of controls, i.e., some fixed controls CF and some temporary controls CV, will be described below, according to various embodiments, with reference to FIGS. 4a, 4b, 5a-5e.

It is worth noting that the temporary controls CV are displayed at different times and sometimes separately from each other, as will be described with particular reference to FIGS. 5a-5e.

Figure 4B:
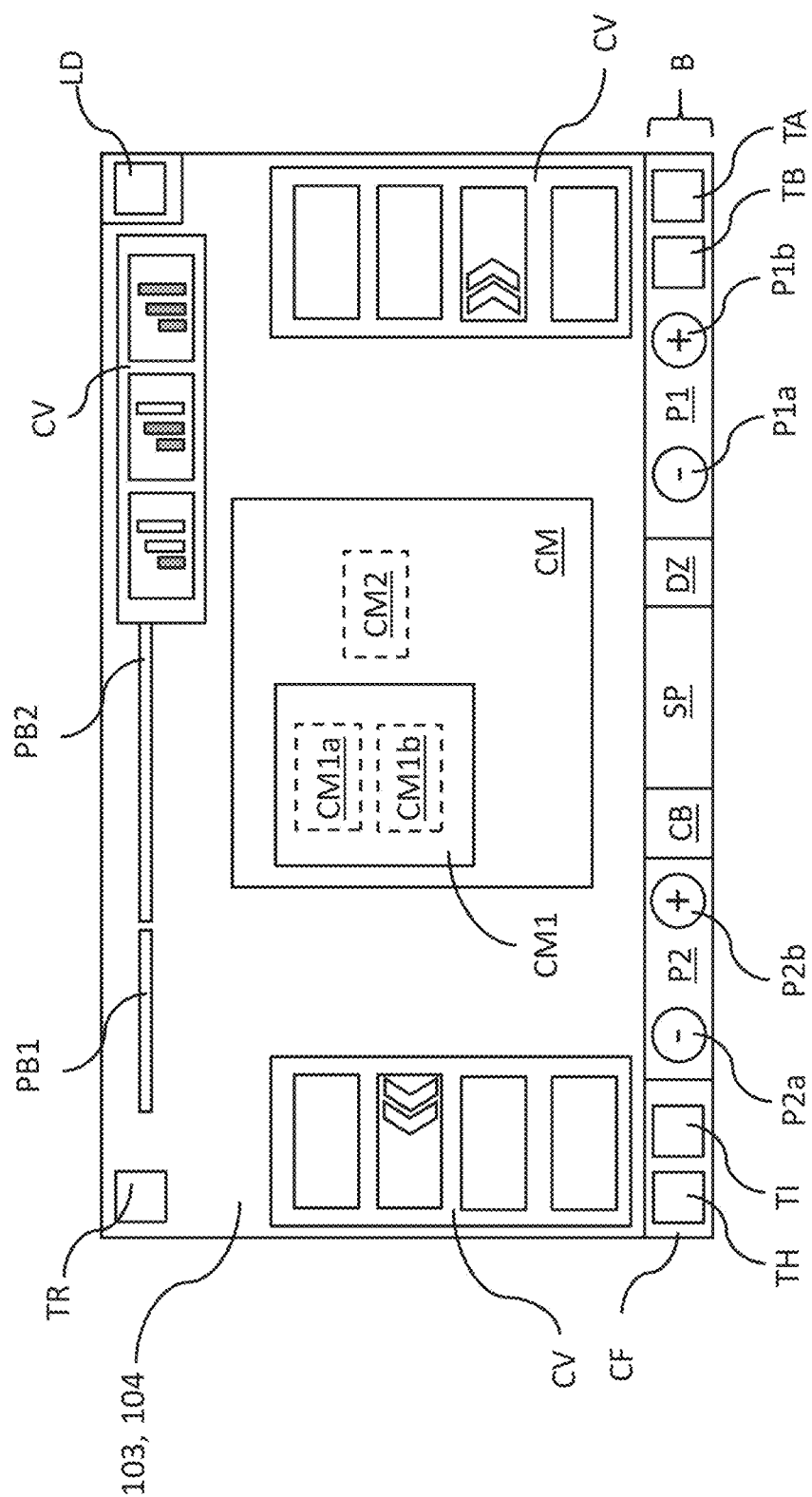
FIG. 4b diagrammatically illustrates a screen of a control interface of an exercise machine which shows different components displayable at the same time in different operating configurations, according to different embodiments.

FIG. 4b shows a summary of some fixed controls CF, already shown in FIG. 4a, and some temporary controls CV distributed in respective portions of the display module 104 of the control interface 103.

Although represented all together in FIG. 4b, some of the temporary controls CV belong to separate operational configurations of the control interface 103 and may therefore not be displayed at the same time by the display module 104, as specified with reference to FIGS. 5a-5e.

According to an embodiment, in combination with any of those described above, the control interface 103 is configured to allow a user to enjoy an audio signal.

Such an audio signal represents the at least one audio component CM1 of a multimedia content CM (whether only an audio of the personal trainer or also a video of the personal trainer) enjoyable by the user during performance of physical activity on the exercise machine 100.

In one embodiment, in combination with the preceding one, the control interface 103 comprises an audio broadcast module 105, e.g., at least one speaker, operatively connected to the data processing unit 101.

In this regard, the control interface 103 is configured to allow a user to enjoy an audio signal by means of the audio broadcast module 105.

According to an embodiment, in combination with any embodiment described above, the control interface 103 is configured to allow a user to enjoy an audio signal through a headset.

In an embodiment, in combination with the preceding one, the control interface 103 comprises a connection socket 106, such as a female jack socket or an equivalent one, configured to allow a wired connection of a user headset to the control interface 103.

In an embodiment, either in combination with or as an alternative to the preceding one, the control interface 103 comprises a data communication module 107 configured to allow a headset of the user to be wirelessly connected to the control interface 103, e.g., through a Bluetooth, NFC, Wi-Fi communication channel, or other equivalent technology.

According to an embodiment, in combination with any of those described above, the exercise machine 100 further comprises a data communication interface 108 operatively connected to the data processing unit 101, configured to allow the exercise machines 100 to transmit and receive data through a data communication network (not shown in the figures), e.g., the Internet network, to which the exercise machine 100 is operatively connected.

The connection of the exercise machine 100 to the data communication network may be wired or wireless.

Turning back to the exercise machine 100, according to an embodiment, the exercise machine 100 is configured so that a multimedia content CM of a personal trainer, preparatory to carrying out a set workout program on the exercise machine 100, is associated with configuration instructions IC of the exercise machine 100 readable by the data processing unit 101 of the exercise machine 100 synchronized with the playing of the multimedia content CM.

The configuration instructions IC of the exercise machine 100 are stored in the memory unit 102 of the exercise machine 100.

In greater detail, the memory unit 102 of the exercise machine is configured to store configuration instructions IC of the exercise machine 100 for each set workout program executable on the exercise machine 100.

The configuration instructions IC are, for example, one or more program codes written in JSON (JavaScript Object Notation).

Along an advancement timeline of the multimedia content, associated with the multimedia content, the configuration instructions IC of the exercise machine 100 define a plurality of set time intervals in which, for each set time interval, the control interface 103 of the exercise machine 100 assumes a respective operating condition adapted to allow the user to interact with the control interface 103 as required by the multimedia content CM in the set time interval of the set workout program.

Such an interaction includes the possibility of varying the level of difficulty of the initial workout or the operating parameters of the exercise machine 100, such as speed and slope if the exercise machine is a treadmill, or resistance if the exercise machine is a bike.

Furthermore, such an interaction includes providing the user with information on the progress of the set workout program, for example when it is necessary to change one or more operating parameters of the exercise machine or suggestions on which controls to operate as indicated in the multimedia content CM.

Each time interval thus corresponds to a phase of the set workout program that the user is following on the exercise machine 100 through the enjoy of the multimedia content CM.

The data processing unit 101 is configured to play the multimedia content CM and to read the configuration instructions IC of the exercise machine 100.

During the enjoy of the multimedia content CM, based on the configuration instructions IC of the exercise machine 100, if a playing time instant of the multimedia content CM falls within a set time interval provided by the configuration instructions IC of the exercise machine 100, the data processing unit 101 is configured to dynamically modify the control interface 103 of the exercise machine 100 to assume a respective operating configuration corresponding to the set time interval reached by the multimedia content CM.

A "dynamic change" of the configuration of the control interface 103 means an update of the configuration of the control interface 103 according to the configuration instructions IC of the control interface 103 readable by the data processing unit 101 during the playing of the multimedia content CM with which the configuration instructions IC are associated.

In a respective operating configuration of the control interface 103, the data processing unit 101 is configured to show to the user through the display module 104 of the control interface 103, temporary controls CV made available by the control interface 103 and enabled to be used by the user through the control interface 103 in said operating configuration.

Indeed, "operating configuration" of the control interface 103 means the display of set temporary controls CV on the display module 104 and, possibly, other graphic components, in a set position and with a set appearance mode on the display module 104, corresponding to the phase of the set workout program that the user must execute as long as the enjoy time instant of the multimedia content CM is comprised in the set time interval corresponding to an operating configuration of the control interface 103.

In a respective operating configuration, the data processing unit 101 is configured to set the exercise machine 100 based on the temporary controls CV made available by the control interface 103 and selected by the user through the control interface 103 in said operating configuration.

In greater detail, the data processing unit 101 is configured to send respective control signals representative of the temporary controls CV selected by the user to one or more components of the exercise machine 100.

Some operational configurations that the control interface 103 may assume according to various embodiments will now be described with reference to FIGS. 4a, 5a-5e.

With reference to FIG. 4a, in an embodiment, at the beginning of the playing of the multimedia content CM, the data processing unit 101, based on the configuration instructions IC being read together with the playing of the multimedia content CM, is configured to modify the control interface 103 to assume a respective operating configuration.

According to this embodiment, in this operating configuration of the control interface 103, the data processing unit 101 is configured to display fixed controls CF of the plurality of controls which may be made available to the user on the display module 104, in addition to the multimedia content CM being played.

In more detail, such fixed controls CF comprise a horizontal control bar B that may be placed at the bottom of the display module 104.

The horizontal control bar B comprises:
- a home button TH to go back to the home screen;
- a settings button TI to go to the settings screen of the exercise machine 100;
- a Bluetooth button TB to set up the Bluetooth connection;
- a volume key TA to set the volume level of the control interface 103;
- a stop/pause button SP;
- a first pair of buttons P1a, P1b to vary the level of a first operating parameter P1 of the exercise machine 100; and
- a second pair of buttons P2a, P2b to vary the level of a second operating parameter P2 of the exercise machine 100 (FIGS. 4a-4b, 5a-5d).

If the exercise machine 100 is a treadmill, the first operating parameter P1 is the speed of the treadmill and the second operating parameter P2 is the slope of the treadmill.

If the exercise machine 100 is a bike, the first operating parameter P1 is resistance.

Figure 5A:
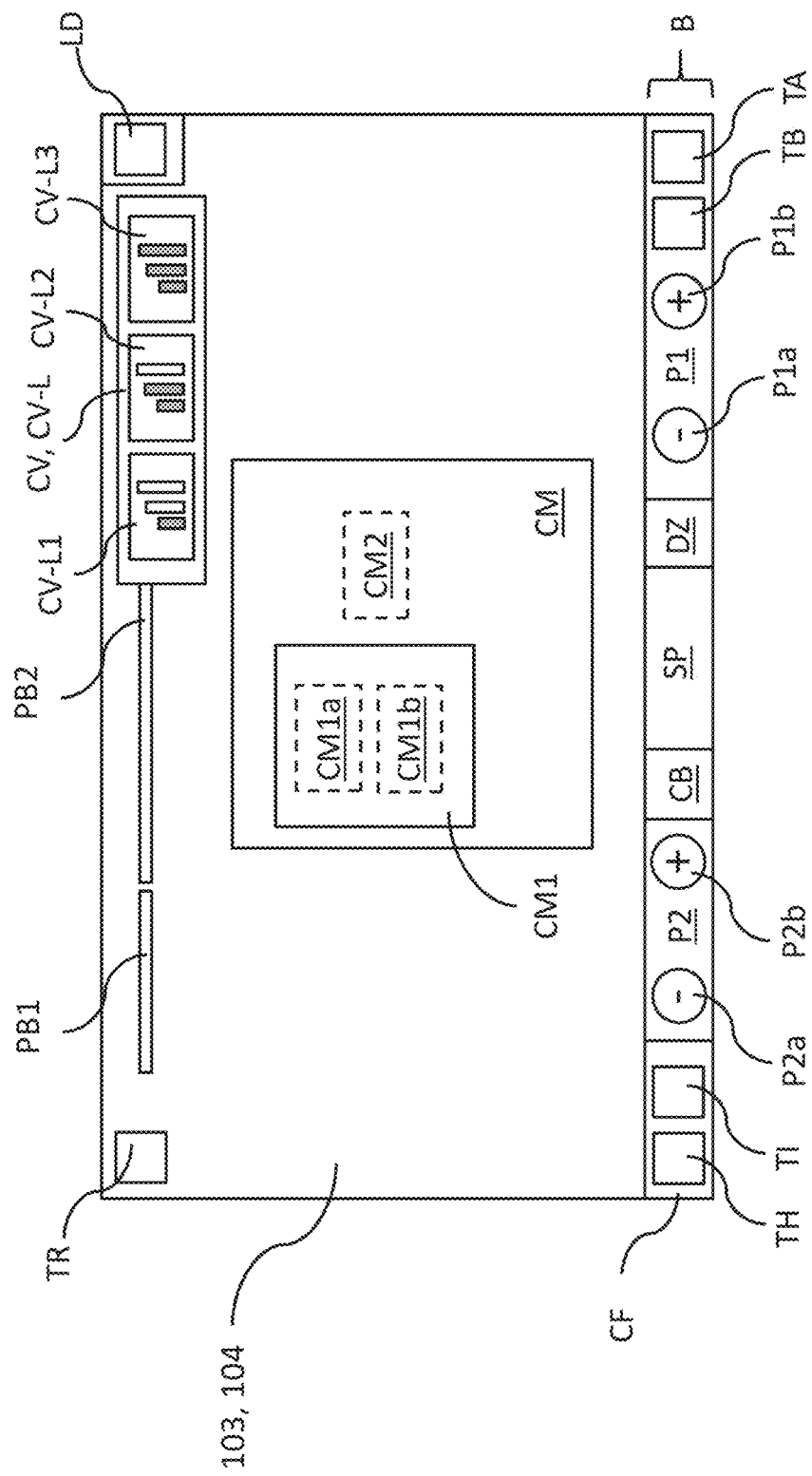
FIGS. 5a-5e diagrammatically illustrate screens of a control interface of an exercise machine in different operating configurations, according to embodiments of the present invention.
Figure 5B:
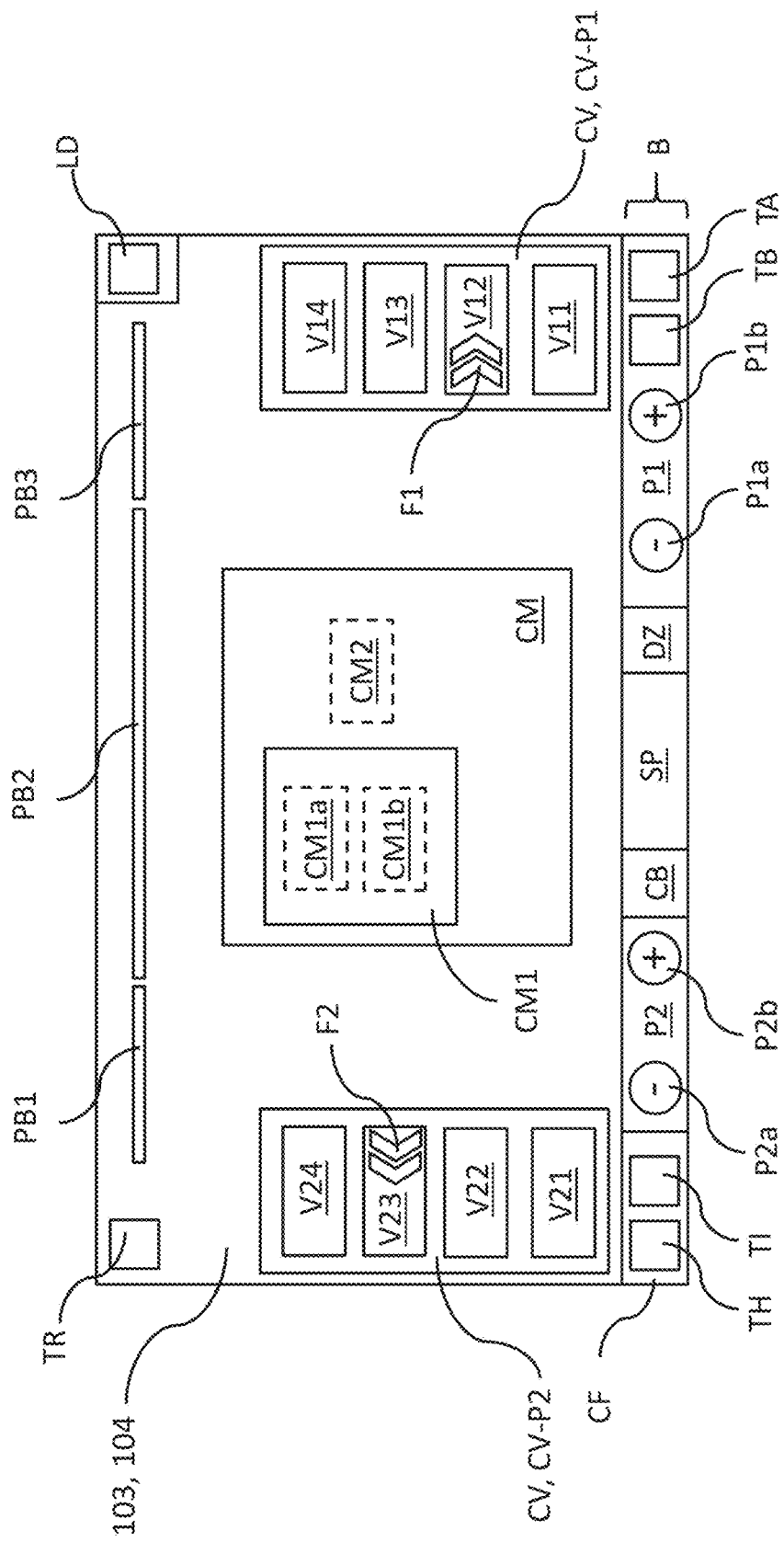
Figure 5C:
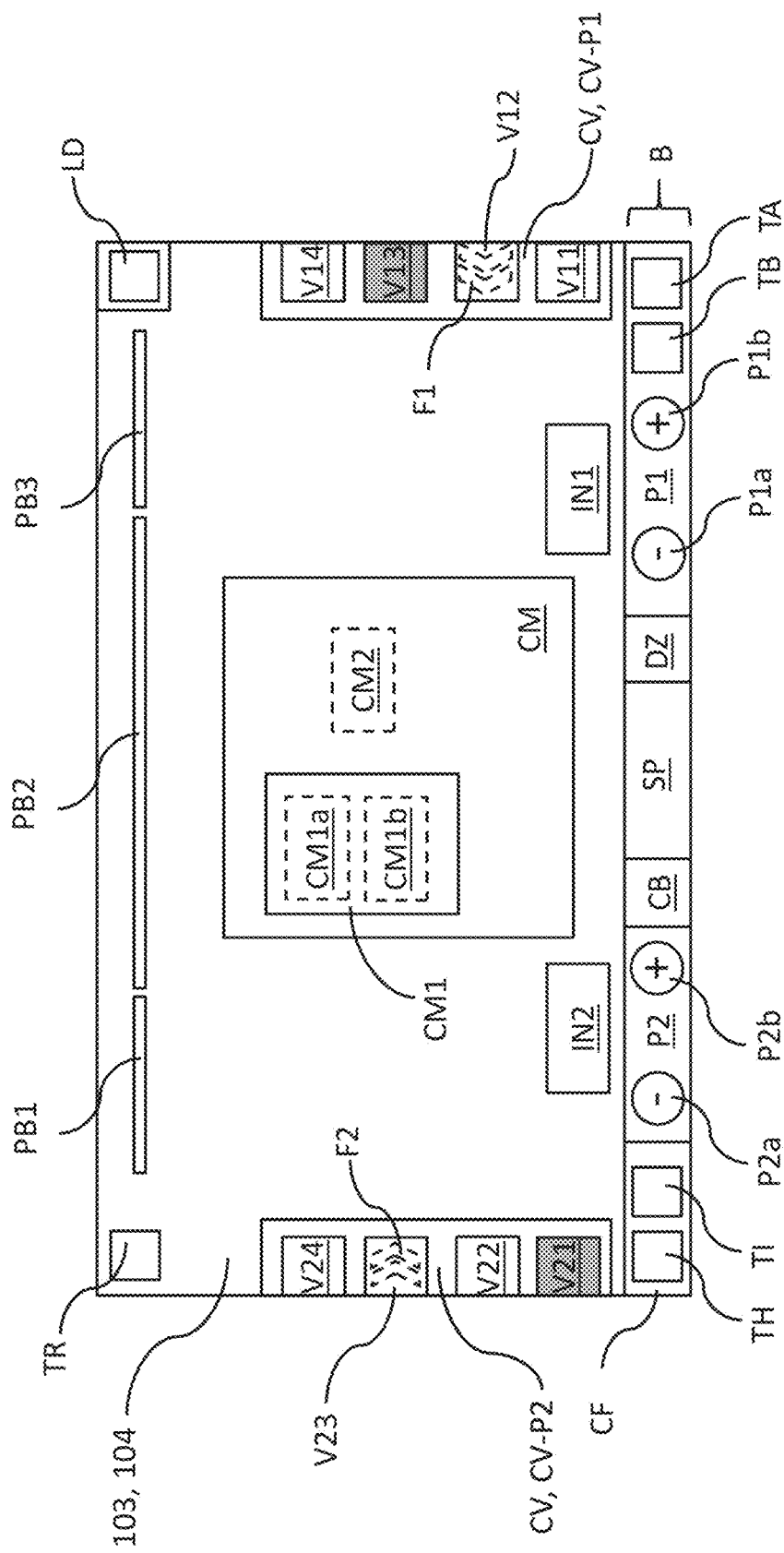
Figure 5D:
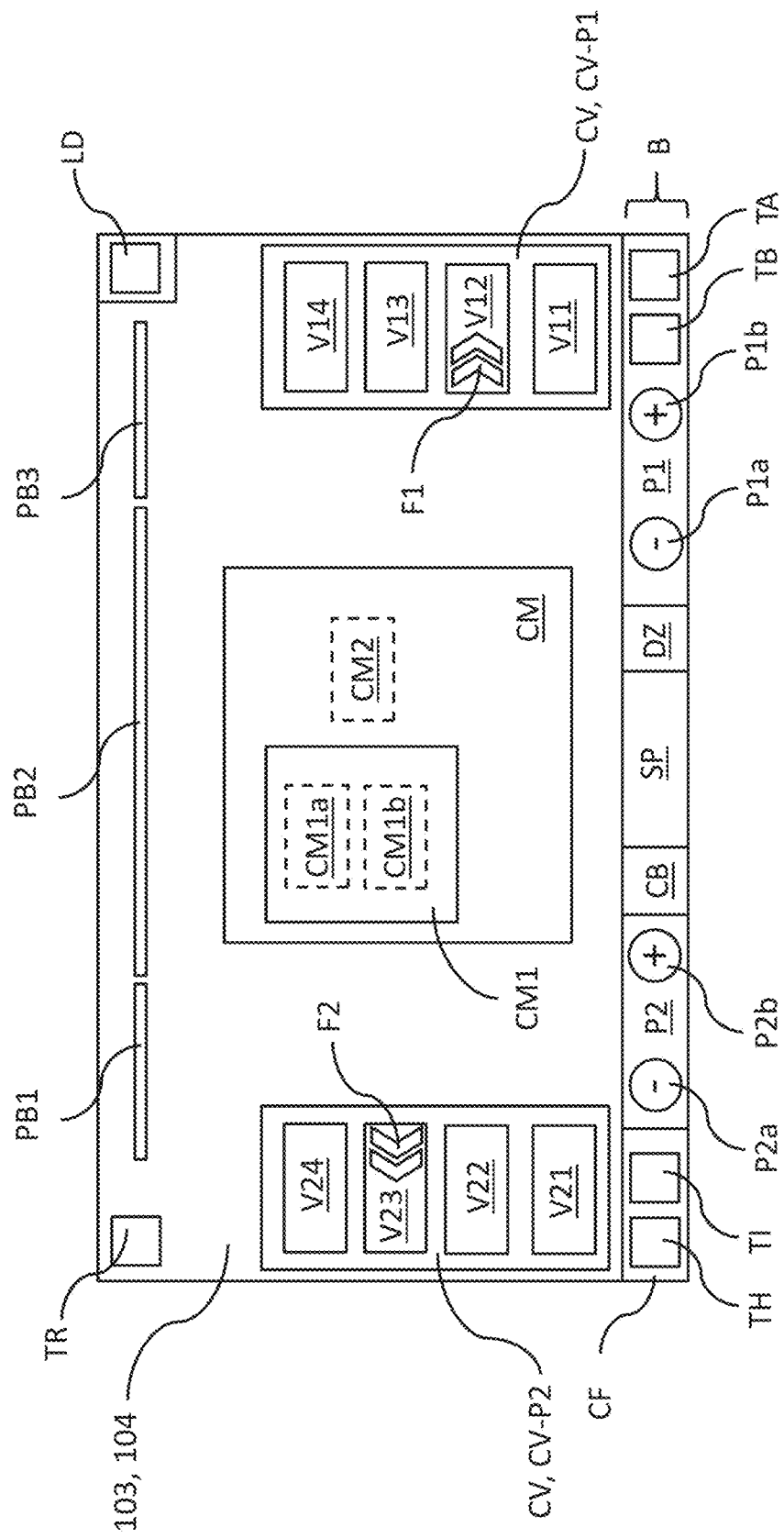
Figure 5E:
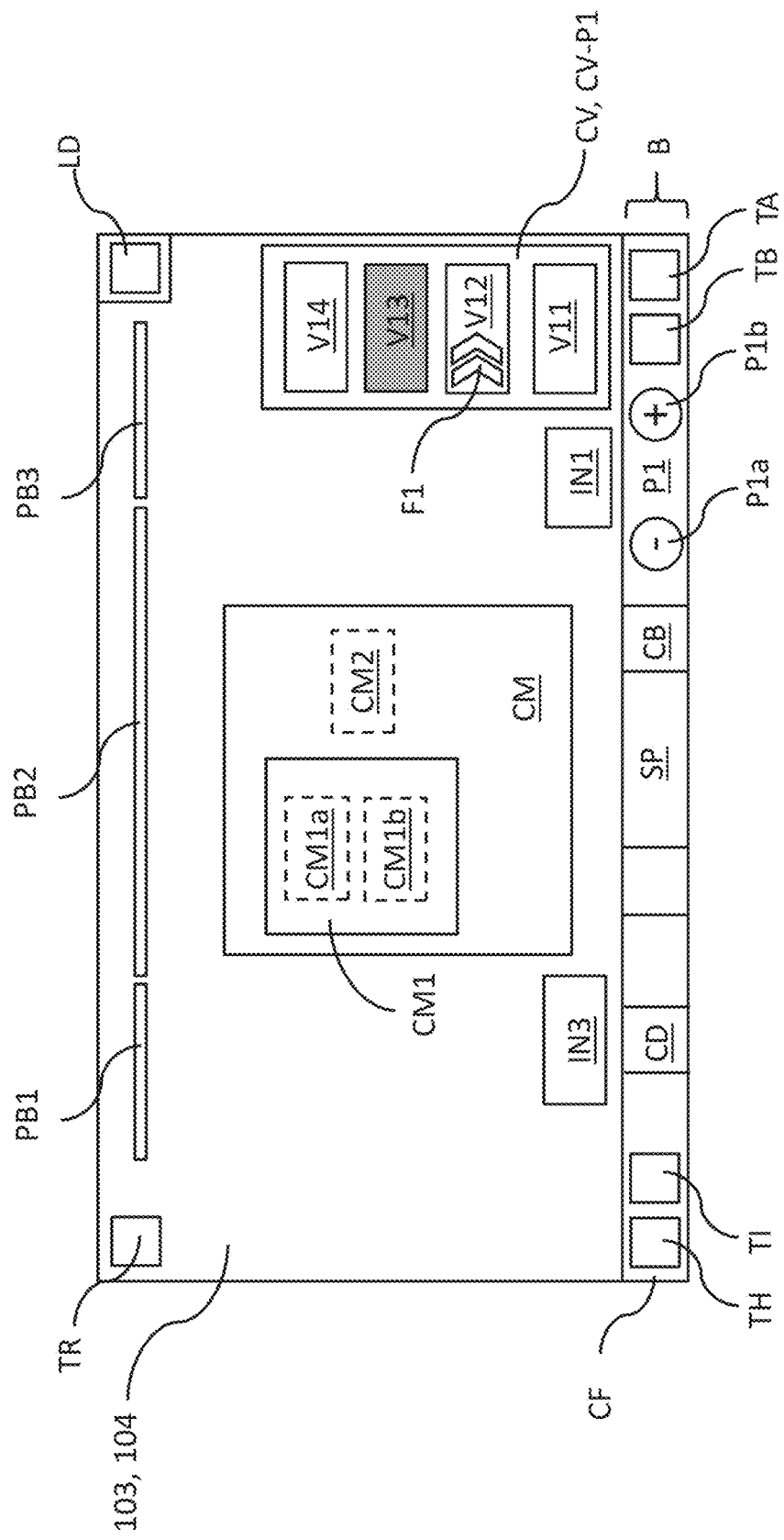

The horizontal control bar B is also configured to show the user, in addition to the current value of the first operating parameter P1 and the current value of the second operating parameter P2 (if present), information, such as burned calories CB and covered distance DZ, if the exercise machine is a treadmill (FIGS. 4a-4b, 5a-5d), burned calories CB and pace CD if the exercise machine is a bike (FIG. 5e).

Referring to FIG. 4a, the display module 104 is configured to provide the user with additional information/controls outside of the horizontal control bar B, such as:
- the remaining time TR to finish the workout;
- a control LD to set the workout difficulty level; and
- a plurality of horizontal time bars PB1-PB3 configured to display the time progression of the workout.

It is worth noting that the control LD can be operated by a user at any time and brings up a menu with workout difficulty levels settable by the user, such as beginner, intermediate and advanced.

Each horizontal time bar of said plurality PB1-PB3 relates to one or more set workout phases, e.g.:
- a first horizontal time bar PB1 relates to a warm-up phase;
- a second horizontal time bar PB2 relates to one or more intense workout phases; and
- a third horizontal time bar PB3 relates to a wind-down phase.

It is worth noting that additional information/controls outside the horizontal control bar B are also shown in FIGS. 4b, 5a-5e.

With reference to FIG. 5a, in an embodiment, in combination with any of the preceding ones, after (e.g., a few seconds after) the start of playing the multimedia content CM, based on the configuration instructions IC being read together with the playing of the multimedia content CM, the data processing unit 101 is configured to modify the control interface 103 to assume a respective operating configuration.

According to this embodiment, in this respective operating configuration, the data processing unit 101 is configured to display on the display module 104 temporary controls CV-L representative of initial workout difficulty levels selectable by the user.

The temporary controls CV-L representative of the initial workout difficulty levels selectable by the user may be displayed by the data processing unit 101 by making such controls enter from one side of the display module 104 and making them scroll horizontally to their definitive position (e.g., top right, as shown in FIG. 5a).

In this manner, only temporary portions of the data display module 104 of the control interface 103 (of the touchscreen type) are enabled to be pressed by the user, preventing the user from changing the initial workout difficulty level when it is not necessary.

Furthermore, the fact that the temporary controls CV-L representative of the initial workout difficulty levels selectable by the user are displayed dynamically advantageously helps the user, even under stress, to immediately locate the controls and promptly follow the selection request suggested by the personal trainer in the multimedia content.

It is worth noting that the temporary controls CV-L representative of initial workout difficulty levels selectable by the user are displayed in the instant of time in which the personal trainer in the multimedia content CM asks the user to select the initial workout difficulty level.

The temporary controls CV-L representative of initial workout difficulty levels selectable by the user comprise:
- a first temporary control CV-L1 to select a first initial workout level, e.g., a beginner level;
- a second temporary control CV-L2 to select a second initial workout difficulty level, e.g., an intermediate level; and
- a third temporary control CV-L3 to select a third initial workout difficult level, e.g., an advanced level.

It is worth noting that at the end of the time interval corresponding to this second operating configuration, in which the user can select an initial workout difficulty level, the data processing unit 101 is configured, if the user has not made any selection, to automatically set the first initial workout difficulty level.

Furthermore, it is worth noting that the data processing unit 101, once the initial workout difficulty level has been set (either as a result of selection by the user or automatically when the time expires), is configured to remove from the display module 104 the temporary controls CV-L representative of workout levels selectable by the user.

With reference to FIG. 5b, in an embodiment, either alternatively or in combination with the preceding one in which the initial workout difficulty level can be selected, the data processing unit 101, based on the configuration instructions IC being read together with the playing of the multimedia content CM, is configured to modify the control interface 103 so that it assumes a respective operating configuration.

According to this embodiment, in this operating configuration, the data processing unit 101 is configured to display on the display module 104 temporary controls CV-P1 representative of values selectable by the user of at least one first operating parameter P1 of the exercise machine 100.

In this embodiment, the temporary controls CV-P1 representative of values selectable by the user of at least one first operating parameter P1 may be displayed by the data processing unit 101 by making such controls enter from one side of the display module 104 and making them scroll horizontally to their definitive position (e.g., the right side of the display module 104).

In an embodiment, in combination with the preceding one, the data processing unit 101, based on the configuration instructions IC read together with the playing of the multimedia content CM, is configured to indicate on the display module 104 which of the temporary controls CV-P1 representative of values selectable by the user of at least one first operating parameter P1 of the exercise machine 100 is suggested by the personal trainer in the multimedia content CM for the phase of the set workout program that the user is performing in the set time interval that the multimedia content CM is at.

Such indication is obtainable by displaying one or more arrows F1, preferably moving or flashing, within the portion of the display module 104 containing the suggested temporary control.

In an embodiment, in combination with the preceding ones in which reference is made to the at least one first operating parameter P1, in this operating configuration, after selection by the user of a value of at least one first operating parameter P1 (which may also be different from that possibly suggested by the personal trainer in the multimedia content CM), the data processing unit 101 is configured to set the exercise machine 100 as a function of the value of the at least one first operating parameter P1 selected by the user.

In an embodiment, in combination with the preceding one, once the user has selected the value of the at least one first operating parameter P1, the data processing unit 101 is configured to indicate which value was selected by the user, e.g., by representing its background in a different color.

In an embodiment, in combination with any of the preceding ones in which the user has selected a value of the at least one first operating parameter P1 and in which an indication is provided on the display module 104 of which among the temporary controls CV-P1 representative of values selectable by the user of at least one first operating parameter P1 of the exercise machine 100 is suggested by the personal trainer in the multimedia content CM, the data processing unit 101, based on the configuration instructions IC read together with the playing of the multimedia content CM, if the value of the at least one first operating parameter P1 that the user has selected is different from the suggested value, is configured to maintain on the display module 104 an indication of which of the temporary controls CV-P1 representative of values selectable by the user of at least one first operating parameter P1 of the exercise machine 100 is suggested by the personal trainer in the multimedia content CM for that phase of the set workout program.

In an embodiment, in combination with any of the preceding ones, in which reference is made to the at least one first parameter P1, in this operating configuration, the data processing unit 101 is further configured to display on the display module 104 temporary controls CV-P2 representative of values selectable by the user of a second operating parameter P2 of the exercise machine 100.

If the exercise machine 100 is a treadmill, the at least one first operating parameter P1, for example, is the speed of the treadmill and the second operating parameter P2, for example, is the slope of the treadmill.

In this embodiment, the temporary controls CV-P1 representative of values selectable by the user of at least one first operating parameter P1 and of the temporary controls CV-P2 representative of values selectable by the user of a second operating parameter P2, by the data processing unit 101, may be displayed by making such controls enter from one side of the display module 104 and making them scroll horizontally to their definitive position (e.g., the right side and on the left side of the display module 104, respectively).

In an embodiment, in combination with the preceding one, the data processing unit 101, based on the configuration instructions IC read together with the playing of the multimedia content CM, is configured to indicate on the display module 104 which of the temporary controls CV-P2 representing values selectable by the user of a second operating parameter P2 of the exercise machine 100 is suggested by the personal trainer in the multimedia content CM for the phase of the set workout program that the user is performing in the set time interval that the multimedia content CM is at.

Such indication is obtainable by displaying one or more arrows F2, preferably moving or flashing, within the portion of the display module 104 containing the suggested temporary control.

In an embodiment, in combination with the preceding ones in which reference is made to the second operating parameter P2, in this operating configuration, after the selection by the user of a value of the second operating parameter P2 (which may also be different from that possibly suggested by the personal trainer in the multimedia content CM), the data processing unit 101 is configured to set the exercise machine 100 as a function of the value of the second operating parameter P2 selected by the user.

In an embodiment, in combination with the preceding one, the data processing unit 101, once the user has selected the value of the second operating parameter P2, is configured to indicate which value was selected by the user e.g., by representing its background in a different color.

In an embodiment, in combination with any of the preceding ones in which the user has selected a value of the second operating parameter P2 and in which an indication is provided on the display module 104 of which of the temporary controls CV-P2 representative of values selectable by the user of a second parameter P2 of the exercise machine 100 is suggested by the personal trainer in the multimedia content CM, the data processing unit 101, based on the configuration instructions IC being read together with the playing of the multimedia content CM, if the value of the second operating parameter P2 that the user has selected is different from the suggested value, is configured to maintain on the display module 104 an indication of which among the temporary controls CV-P2 representative of values selectable by the user of a second operating parameter P2 of the exercise machine 100 is suggested by the personal trainer in the multimedia content CM for that phase of the set workout program.

It is worth noting that, in the embodiments described above, only temporary portions of the display module 104 of the control interface 103 (of the touchscreen type) are enabled to be pressed by the user, preventing the user from changing the operating parameters of the exercise machine 100 when it is not necessary.

Furthermore, the fact that display of the temporary controls CV-P1 representative of values selectable by the user of at least one first operating parameter P1 and the temporary controls CV-P2 representative of values selectable by the user of a second operating parameter P2 of the exercise machine 100 occurs dynamically advantageously helps the user, even under stress, to immediately identify the controls and to promptly follow the selection request suggested by the personal trainer in the multimedia content CM.

Furthermore, the presence of indicators (arrows F1 and F2) which highlight the values suggested by the personal trainer facilitates the user in setting the exercise machine 100 during the workout.

It is worth noting that the temporary controls CV-P1 representative of values selectable by the user of at least one first operating parameter P1 and the temporary controls CV-P2 representative of values selectable by the user of a second operating parameter P2 are displayed in the time instant in which the personal trainer asks the user to set the value of the at least one first operating parameter P1 and the value of the second operating parameter P2 in the multimedia content CM.

The temporary controls CV-P1 representative of values selectable by the user of at least one first operating parameter P1 comprise:
- a first temporary control V11 to select a first value of the first operating parameter P1, e.g., a speed value of the treadmill corresponding to a walk, "walk" (e.g., 6 km/h);
- a second temporary control V12 to select a first value of the second operating parameter P1, e.g., a speed value of the treadmill corresponding to a slow pace run, "jog" (e.g., 9 km/h);
- a third temporary control V13 to select a third value of the first operating parameter P1, e.g., a speed value of the treadmill corresponding to a normal pace run, "run" (e.g., 12 km/h); and
- a fourth temporary control V14 to select a fourth value of the first operating parameter P1, e.g., a speed value of the treadmill corresponding to a fast pace run, "sprint" (e.g., 15 km/h).

It is worth noting that the selectable values of the first operating parameter P1 are suggested by the data processing unit 101 as a function of the selected initial workout difficulty level.

The temporary controls CV-P2 representative of values selectable by the user of a second operating parameter P2 comprise:
- a first temporary control V21 to select a first value of the second operating parameter P2, e.g., a slope value of the treadmill equal to 0%, "flat";
- a second temporary control V22 to select a second value of the second operating parameter P2, e.g., a slope value corresponding to a hill climb, "hill" (e.g., 2%);
- a third temporary control V23 to select a third value of the second operating parameter P2, e.g., a climb slope value, "climb" (e.g., 4%); and
- a fourth temporary control V24 to select a fourth value of the second operating parameter P2, e.g., an extreme slope value, "top" (e.g., 6%).

It is also worth noting that the selectable values of the second operating parameter P2 are suggested by the data processing unit 101 as a function of the selected initial workout difficulty level.

In an embodiment, in combination with the preceding ones in which reference is made to the at least one first parameter P1, at the end of the time interval corresponding to this operating configuration, in which the user can select a value of the at least one first operating parameter P1, the data processing unit 101 is configured, if the user has not made any selection, to maintain the value previously manually set by the user as the value of the at least one first operating parameter P1.

In an embodiment, in combination with the preceding ones in which reference is made to the at least one first parameter P1 and alternatively to the preceding one, at the end of the time interval corresponding to this operating configuration, in which the user can select a value of the at least one first operating parameter P1, the data processing unit 101 is configured, if the user has not made any selection, to automatically set the value of the at least one first operating parameter P1 suggested by the personal trainer.

In a further embodiment, in combination with any of the preceding ones in which reference is made to the second parameter P2, at the end of the time interval corresponding to this operating configuration, in which the user can select a value of the second operating parameter P2, the data processing unit 101 is configured, if the user has not made any selection, to maintain the value previously manually set by the user as a value of the second operating parameter P2.

In an embodiment, in combination with the preceding ones in which reference is made to the second operating parameter P2 and alternatively to the preceding one, at the end of the time interval corresponding to this operating configuration, in which the user can select a value of the second operating parameter P2, the data processing unit 101 is configured, if the user has not made any selection, to automatically select the value of the second operating parameter P2 suggested by the personal trainer.

In an embodiment, in combination with the preceding one and shown in FIG. 5c, the data processing unit 101, once the user has selected the value of the at least one first operational parameter P1 (which may also be different from the value possibly suggested by the personal trainer in the multimedia content CM), is configured to shift the temporary controls CV-P1 representative of values selectable by the user of at least one first operating parameter P1 towards the outside of the display module 104 so that they are partially visible.

According to further embodiments, in combination with the preceding one, the data processing unit 101, once the user has selected the value of the at least one first operating parameter P1 (which may also be different from the value possibly suggested by the personal trainer in the multimedia content CM), is configured to shift the temporary controls CV-P1 representative of values selectable by the user of at least one first operating parameter P1 towards the outside of the display module 104 so that they are partially visible, indicating the set value and/or leaving the temporary controls enabled to be pressed.

In this manner, the user always has an optimal view of the multimedia content CM and of the set operating parameter value and/or can change the operating parameter value.

In an embodiment, in combination with the preceding one shown in FIG. 5c, the data processing unit 101, once the user has selected the value of the second operating parameter P2 (which may also be different from the value possibly suggested by the personal trainer in the multimedia content CM), is configured to shift the temporary controls CV-P2 representative of values selectable by the user of a second operating parameter P2 towards the outside of the display module 104 at the same time as the temporary controls CV-P1 representative of values selectable by the user of at least one first operating parameter P1 so that they are partially visible.

According to further embodiments, in combination with the preceding one, the data processing unit 101, once the user has selected the value of the second operating parameter P2 (which may also be different from the value possibly suggested by the personal trainer in the multimedia content CM), is configured to shift the temporary controls CV-P2 representative of values selectable by the user of a second operating value P2 towards the outside of the display module 104 at the same time as the temporary values CV-P1 representative of values selectable by the user of at least one first operating parameter P1 so that they are partially visible, indicating the set values and/or leaving the respective temporary controls enabled to be pressed.

In this manner, the user always has an optimal view of the multimedia content CM and of the set operating parameter value and/or can change the operating parameter value.

As shown in FIG. 5c, an indication of which values were selected by the user can be obtained by representing the background of the respective temporary controls in a different color than any other temporary control.

In an embodiment, in combination with the preceding one, the data processing unit 101 is configured to shift laterally towards the inside of the display module 104, restoring the display shown in FIG. 5b, temporary controls CV-P1 representative of values selectable by the user of at least one first operating parameter P1 (with an indication of which value was selected by the user) in response to a touch (tap) of the user anywhere on the display module 104.

In an embodiment, in combination with the preceding one, the data processing unit 101 is configured to shift the temporary controls CV-P2 representative of values selectable by the user of a second operating parameter P2 laterally towards the inside of the display module 104, restoring the display shown in FIG. 5b, at the same time as the temporary controls CV-P1 representative of values selectable by the user of at least one first operating parameter P1 (with the indication of which values were selected by the user) in response to a touch (tap) performed by the user anywhere on the display module 104.

In this manner, the user can go back to the temporary controls to set the value of the operating parameters of the exercise machine 100 again if necessary and with a simple tap.

Again, with reference to FIG. 5c, according to an embodiment, shown by dashed lines, the data processing unit 101 is configured to indicate the value of temporary controls (first operating parameter P1 and second operating parameter P2) suggested by the trainer, e.g., by one or more arrows F1 and F2, moving or flashing, even if such values are not the ones selected by the user, represented with a background of a different color from the other temporary controls.

In an embodiment, in combination with any one described above with reference to FIG. 5c, the data processing unit 101 is further configured to display on the display module 104 a first indicator IN1 of the fact that the exercise machine 100 is adjusting (setting) the value of the at least one first operating parameter P1 to the value selected by the user.

In an embodiment, in combination with the preceding one, the data processing unit 101 is further configured to display on the display module 104 a second indicator IN2 of the fact that the exercise machine 100 is adjusting (setting) the value of the second operating parameter P2 to the value selected by the user.

With reference to FIG. 5d, in an embodiment, in combination with any of the preceding ones, before (e.g., 5 seconds before) the start of one of the one or more set workout phases, the data processing unit 101, based on the configuration instructions IC read together with the playing of the multimedia content CM, is configured to modify the control interface 103 to assume a further operating configuration.

According to this further embodiment, in this further operating configuration, the data processing unit 101 is configured to display on the display module 104 temporary controls CV-P1 representative of values selectable by the user of at least one first operating parameter P1 of the exercise machine 100 (e.g., the speed of the treadmill).

Also in this embodiment, the temporary controls CV-P1 representative of values selectable by the user of at least one first operating parameter P1 may be displayed by the data processing unit 101 by making such controls enter from one side of the display module 104 and making them scroll horizontally to their definitive position (e.g., the right side of the display module 104).

In an embodiment, in combination with the preceding one, the data processing unit 101, based on the configuration instructions IC read together with the playing of the multimedia content CM, is configured to indicate on the display module 104 which of the temporary controls CV-P1 representing values selectable by the user of at least one first operating parameter P1 of the exercise machine 100 is suggested by the personal trainer in the multimedia content CM for the phase of the set workout program that the user is about to perform in the set time interval in which the multimedia content CM is about to enter.

Such indication is obtainable by displaying one or more arrows F1, preferably moving or flashing, within the portion of the data display module 104 containing the suggested temporary control.

In an embodiment, in combination with the preceding ones in which reference is made to the at least one first operating parameter P1, in this operating configuration, after the selection by the user of a value of the at least one first operating parameter P1 (which may also be different from that possibly suggested by the personal trainer in the multimedia content CM), the data processing unit 101 is configured to set the exercise machine 100 as a function of the value of the at least one first operating parameter P1 selected by the user.

In an embodiment, in combination with any preceding one, in this further operating configuration, the data processing unit 101 is further configured to display on the display module 104 temporary controls CV-P2 representative of values selectable by the user of a second operating parameter P2 of the exercise machine 100 (e.g., the slope of a treadmill).

In this embodiment, the temporary controls CV-P1 representative of values selectable by the user of at least one first operating parameter P1 and of the temporary controls CV-P2 representative of values selectable by the user of a second operating parameter P2 may be displayed by the data processing unit 101 by making such controls enter from one side of the display module 104 and making them scroll horizontally to their definitive position (e.g., the right side and on the left side of the display module 104, respectively).

In an embodiment, in combination with the preceding one, the data processing unit 101, based on the configuration instructions IC read together with the playing of the multimedia content CM, is configured to indicate on the display module 104 which of the temporary controls CV-P2 representing values selectable by the user of a second operating parameter P2 of the exercise machine 100 is suggested by the personal trainer in the multimedia content CM for the phase of the set workout program that the user is performing in the set time interval that the multimedia content CM is at.

Such an indication is obtainable by displaying one or more arrows F2, preferably moving or flashing, within the portion of the data display module 104 containing the suggested temporary control.

In an embodiment, in combination with the preceding ones in which reference is made to the second operating parameter P2, in this operating configuration, after the selection by the user of a value of the second operating parameter P2 (which may also be different from that possibly suggested by the personal trainer in the multimedia content CM), the data processing unit 101 is configured to set the exercise machine 100 as a function of the value of the second operating parameter P2 selected by the user.

It is further worth noting that the display of the temporary controls CV-P1 representative of values selectable by the user of at least one first operating parameter P1 (and of the temporary controls CV-P2 representative of values selectable by the user of a second operating parameter P2) occurs, based on the configuration instructions IC read together with the playing of the multimedia content CM, either before or at the same time of the time instant of the multimedia content CM in which the personal trainer asks the user to set the value of the at least one first operating parameter P1 (and the value of the second operating parameter P2).

Therefore, the user is advantageously informed about the next workout phase of the set workout program before it starts.

The temporary controls CV-P1 representative of values selectable by the user of at least one first operating parameter P1 (and the temporary controls CV-P2 representative of values selectable by the user of a second operating parameter P2) have already been described above with reference to FIG. 5b.

It is worth noting that the selectable values of the at least one first operating parameter P1 (and of the second operating parameter P2) are suggested by the data processing unit 101 as a function of the selected initial workout difficulty level.

In this embodiment, if the user does not select any value of the at least one first operating parameter P1 (or a value of the second operating parameter P2), the data processing unit 101 is configured to maintain the value of the at least one first operating parameter P1 and the value of the second operating parameter P2 previously set manually by the user.

In an embodiment, the data processing unit 101 is configured to remove from the display module 104 both the temporary controls CV-P1 representative of values selectable by the user of at least one first operating parameter P1 and the temporary controls CV-P2 representative of values selectable by the user of a second operating parameter P2 in response to a tap performed by the user anywhere on the display module 104 if the user decides not to make any selection.

The further advantages of this fourth operating configuration are similar to those of the operating configuration described with reference to FIGS. 5b and 5c, so will not be repeated.

If the exercise machine 100 is a bike, the same operating configurations of the control interface 103 already described above with reference to FIGS. 4a, 5a and 5b apply with the simplification that the operating parameter selectable by the user, in the case of a bike, is only one, i.e., the resistance.

With reference to FIG. 5e, if the exercise machine 100 is a bike, in an embodiment, after the setting of the initial workout difficulty level, continuing the playing of the multimedia content CM, the data processing unit 101, based on the configuration instructions IC being read together with the playing of the multimedia content CM, is configured to cause the control interface 103 to assume a further operating configuration.

According to this embodiment, in this further operating configuration, the data processing unit 101 is configured to display on the display module 104 temporary controls CV-P1 representative of values selectable by the user of at least one first operating parameter P1 of the exercise machine 100.

In this embodiment, the temporary controls CV-P1 representative of values selectable by the user of at least one first operating parameter P1 may be displayed, by the data processing unit 101, by making such controls enter from one side of the display module 104 and making scroll horizontally to their definitive position (e.g., the right side of the display module 104).

In an embodiment, in combination with the preceding one, the data processing unit 101, based on the configuration instructions IC read together with the playing of the multimedia content CM, is configured to indicate on the display module 104 which of the temporary controls CV-P1 representative values selectable by the user of at least one first operating parameter P1 of the exercise machine 100 is suggested by the personal trainer in the multimedia content CM for the phase of the set workout program that the user is performing in the set time interval that the multimedia content CM is at.

Such indication is obtainable by displaying one or more arrows F1, preferably moving or flashing, within the portion of the data display module 104 containing the suggested temporary control.

In an embodiment, in combination with the preceding ones in which reference is made to the at least one first operating parameter P1, in this operating configuration, after the selection by the user of a value of the at least one first operating parameter P1 (which may also be different from that possibly suggested by the personal trainer in the multimedia content CM), the data processing unit 101 is configured to set the exercise machine 100 as a function of the value of the at least one first operating parameter P1 selected by the user.

In an embodiment, in combination with the preceding one, once the user has selected the value of the at least one first operating parameter P1, the data processing unit 101 is configured to indicate which value was selected by the user, e.g., by representing its background in a different color.

In an embodiment, in combination with any of the preceding ones in which the user has selected a value of the at least one first operating parameter P1 and in which an indication is provided on the display module 104 of which among the temporary controls CV-P1 representative of values selectable by the user of at least one first operating parameter P1 of the exercise machine 100 is suggested by the personal trainer in the multimedia content CM, the data processing unit 101, based on the configuration instructions IC read together with the playing of the multimedia content CM, if the value of the at least one first operating parameter P1 that the user has selected is different from the suggested value, is configured to maintain on the display module 104 an indication of which of the temporary controls CV-P1 representative of values selectable by the user of at least one first operating parameter P1 of the exercise machine 100 is suggested by the personal trainer in the multimedia content CM for that phase of the set workout program.

In this embodiment, only temporary portions of the data display module 104 of the control interface 103 (of the touchscreen type) are enabled to be pressed by the user, preventing the user from changing the initial workout difficulty level when not necessary.

Furthermore, the fact that the temporary controls CV-P1 representative of the values selectable by the user of at least one first operating parameter P1 of the exercise machine 100 are displayed dynamically advantageously helps the user immediately locate the controls even under stress and promptly follow the selection request suggested by the personal trainer in the multimedia content CM.

Furthermore, the presence of indicators (arrows F1), which highlight the values suggested by the personal trainer, facilitate the user in setting up the exercise machine 100 during the workout.

If the exercise machine 100 is a bike, the at least one first operating parameter P1 is, for example, resistance.

In this embodiment, the temporary controls CV-P1 representative of values selectable by the user of at least one first operating parameter may be displayed by the data processing unit 101 by making such controls enter from one side of the display module 104 and making them scroll horizontally to their definitive position (e.g., the right side of the display module 104).

It is worth noting that the display of temporary controls CV-P1 representing values selectable by the user of at least one first operating parameter P1 occurs in the time instant in which in the multimedia content CM the personal trainer asks the user to set the value of the at least one first operating parameter P1.

The temporary controls CV-P1 representative of values selectable by the user of at least one first operating parameter P1 comprise:

- a first temporary control V11 to select a first value of the first operating parameter P1, e.g., a first value of the resistance corresponding to the flat land, "flat";
- a second temporary control V12 to select a second value of the first operating parameter P1, e.g., a resistance value corresponding to a hill climb, "hill" (e.g., 10);
- a third temporary control V13 to select a third value of the first operating parameter P1, e.g., a resistance value corresponding to a climb, "climb" (e.g., 15); and
- a fourth temporary control V14 to select a fourth value of the first operating parameter P1, e.g., an extreme slope value, "top" (e.g., 20).

In an embodiment, in combination with the preceding ones in which reference is made to the at least one first parameter P1, at the end of the time interval corresponding to this further operating configuration, in which the user can select a value of the at least one first operating parameter P1, the data processing unit 101 is configured, if the user has not made any selection, to maintain as a value of the at least one first operating parameter P1 the one previously manually set by the user.

In an embodiment, in combination with the preceding ones in which reference is made to the at least one first parameter P1 and alternatively to the preceding one, at the end of the time interval corresponding to this operating configuration, in which the user can select a value of the at least one first operating parameter P1, the data processing unit 101 is configured, if the user has not made any selection, to automatically set the value of the at least one first operating parameter P1 suggested by the personal trainer.

In an embodiment, in combination with the preceding ones and already shown in FIG. 5c (also valid if the exercise machine 100 is a bike), the data processing unit 101, once the user has selected the value of the at least one first operational parameter P1 (which may also be different from the value possibly suggested by the personal trainer in the multimedia content CM), is configured to shift the temporary controls CV-P1 representative of values selectable by the user of at least one first operating parameter P1 towards the outside of the display module 104 so that they are partially visible.

According to further embodiments, in combination with the preceding one, already shown in FIG. 5c (valid also if the exercise machine 100 is a bike), the data processing unit 101, once the user has selected the value of the at least one first operating parameter P1 (which may also be different from the value possibly suggested by the personal trainer in the multimedia content), is configured to shift the temporary controls CV-P1 representative of values selectable by the user of the at least one first operating parameter P1 towards the outside of the display module 104 so that they are partially visible, indicating the set value and/or leaving the respective temporary controls enabled to be pressed.

In this manner, the user always has an optimal view of the multimedia content CM and possibly of the set operating parameter value and/or can still change the operating parameter value.

As already shown in FIG. 5c, the indication of which value was selected by the user can be obtained by representing the background of the respective temporary control in a different color than any other temporary control.

In an embodiment, in combination with the preceding one, the data processing unit 101 is configured to shift laterally towards the inside of the display module 104, restoring the display shown in FIG. 5e, some temporary controls CV-P1 representative of values selectable by the user of at least one first operating parameter P1 (with an indication of which of the values was selected by the user) in response to a touch (tap) of the user anywhere on the display module 104.

In this manner, the user can go back to the temporary controls to set the value of the first operating parameters P1 of the exercise machine 100 again if necessary and with a simple tap.

In an embodiment, shown in FIG. 5e, in combination with the preceding one, the data processing unit 101 is further configured to display on the display module 104 a first indicator IN1 of the fact that the exercise machine 100 is adjusting (setting) the value of the at least one first operating parameter P1 to the value selected by the user.

Furthermore, in an embodiment shown in FIG. 5e and in combination with the preceding one, the data processing unit 101 is configured to display on the display module 104 a further indicator IN3 of a pace reference value CD to be maintained during workout.

In FIG. 5e, such an additional indicator IN3 is shown at the pace CD of the horizontal control bar B.

Figure 6:
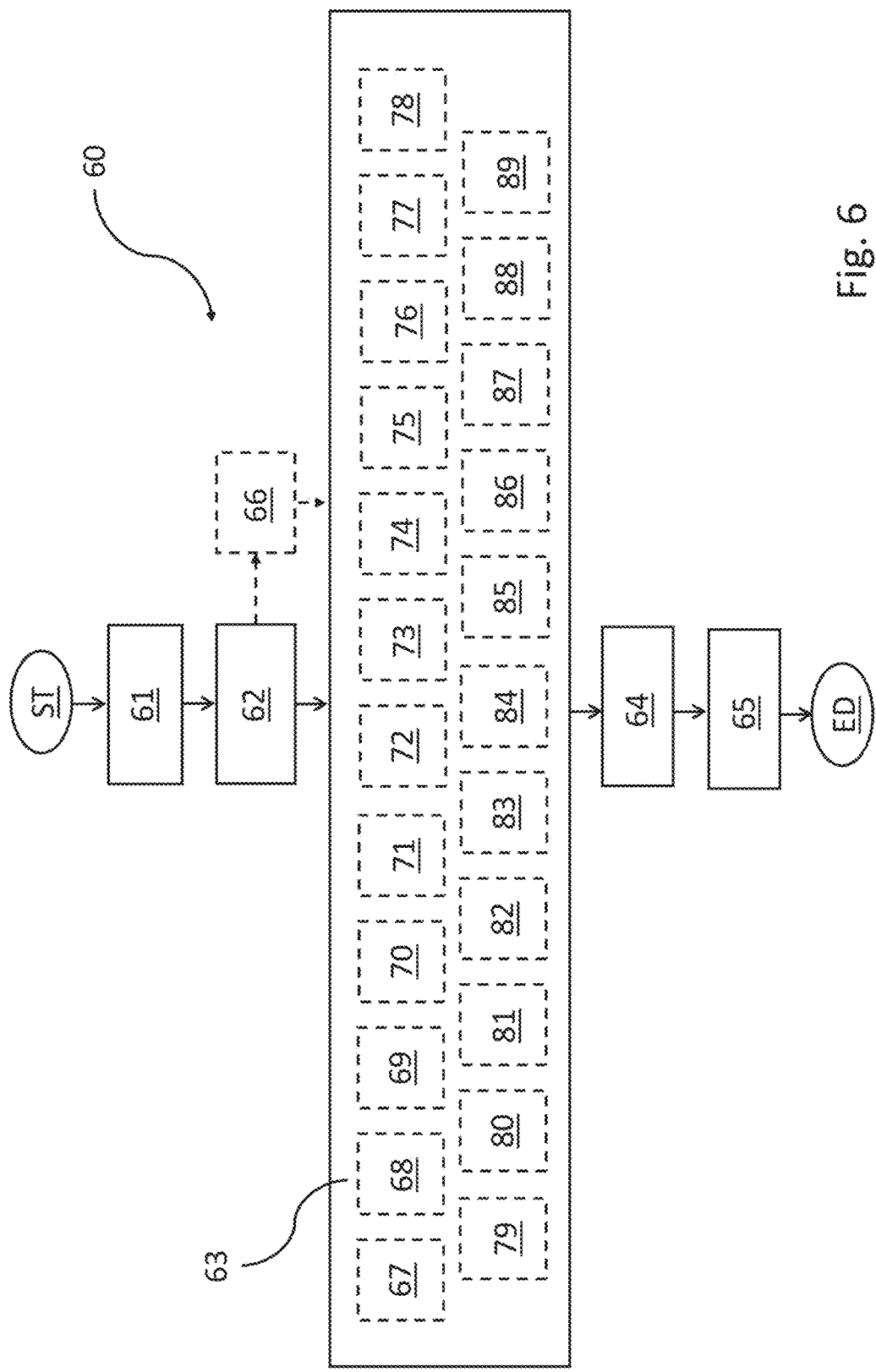
FIG. 6 shows, by means of a block chart, a method for controlling a control interface of an exercise machine during the enjoy of a multimedia content, according to an embodiment of the present invention.

With reference now also to FIG. 6, a method 60 for controlling a control interface of an exercise machine during the enjoy of a multimedia content, hereinafter also control method or simply method, is now described.

The method 60 comprises a symbolic step of starting ST.

The method 60 comprises a step of providing 61 a multimedia content CM of a personal trainer preparatory to performing a set workout program on the exercise machine 100, which can be enjoyed by a user through a control interface 103 of the exercise machine 100.

The multimedia content CM and the control interface 103 of the exercise machine 100 have been described above.

The method 60 further comprises a step of associating 62 configuration instructions IC of the exercise machine 100 with the multimedia content CM which can be read by a data processing unit 101 of the exercise machine 100, synchronized with playing of the multimedia content CM.

The configuration instructions IC and the data processing unit 101 have been described above.

The method 60 further comprises, during the enjoy of the multimedia content CM, if a playing time instant falls within a set time interval provided by the configuration instructions IC of the exercise machine 100, a step of dynamically modifying 63, by the data processing unit 101 of the exercise machine 100, based on the configuration instructions IC of the exercise machine 100, the control interface 103 of the exercise machine 100 so that it assumes a respective operating configuration corresponding to the set time interval reached by the multimedia content CM.

The definition of the operating configuration of the control interface 103 of the exercise machine 100 has been provided above.

The method 60 further comprises a step of showing 64 the user, by the data processing unit 101 through the control interface 103 of the exercise machine 100, temporary controls CV made available by the control interface 103 and enabled to be used by the user through the control interface 103 in the operating configuration.

The method 60 further comprises a step of setting 65, by the data processing unit 101, the exercise machine 100 based on the temporary controls CV made available by the control interface 103 and selected by the user through the control interface 103 in the operating configuration.

In greater detail, the data processing unit 101 is configured to send one or more respective control signals representative of temporary controls CV selected by the user to one or more components of the exercise machine 100.

According to an embodiment, shown with a dashed line in FIG. 6, the method 60 comprises, at the beginning of the playing of the multimedia content CM, a step of dynamically modifying 66, by the data processing unit 101, the control interface 103 based on the configuration instructions IC read together with the playing of the multimedia content CM so that it assumes a respective operating configuration in which to display fixed controls CF of a plurality of controls which are made available to the user on a display module 104 of the control interface 103.

Such fixed controls CF were described above, both if the exercise machine 100 is a treadmill and if the exercise machine 100 is a bike.

According to an embodiment, in combination with the preceding ones, after the beginning of the playing of the multimedia content CM (e.g. a few seconds after) the step of dynamically modifying 63 is performed, by the data processing unit 101, based on the configuration instructions IC read together with the playing of the multimedia content CM, to modify the control interface 103 so that it assumes a respective operating configuration in which to display temporary controls CV-L representative of the initial workout difficulty levels selectable by the user on the display module 104 of the control interface 103.

The temporary controls CV-L representative of initial workout difficulty levels selectable by the user and their display modes were described above.

In an embodiment, in combination with the preceding one, the step of modifying 63 further comprises a step of automatically setting 67, at the end of the time interval corresponding to the operating configuration in which the user can select a first initial workout difficulty level, by the data processing unit 101, if the user has not made any selection, a first initial workout difficulty level.

In an embodiment, in combination with the preceding ones, the step of dynamically modifying 63 comprises a step of removing 68, by the data processing unit 101, the temporary controls CV-L representative of the initial workout levels selectable by the user from the display module 104 once the initial workout level has been set.

In an embodiment, either alternative or in combination with any of the preceding ones, the step of dynamically modifying 63 is performed, by the data processing unit 101, based on the configuration instructions IC of the exercise machine 100 read together with the playing of the multimedia content CM, to modify the control interface 103 so that it assumes a respective operating configuration to display temporary controls CV-P1 representative of values selectable by the user of at least one first operating parameter P1 of the exercise machine 100 on the display module 104.

Temporary controls CV-P1 representative of values selectable by the user of at least a first operating parameter P1 of the exercise machine 100 and their display mode were described above, if the exercise machine 100 is a treadmill and if the exercise machine is a bike.

In an embodiment, in combination with the preceding one, the step of dynamically modifying 63 further comprises a step of indicating 69 on the display module 104, by the data processing unit 101, based on the configuration instructions IC of the exercise machine 100 read together with the playing of the multimedia content CM, which of the temporary controls CV-P1 representative of values selectable by the user of at least one first operating parameter P1 of the exercise machine 100 is suggested by the personal trainer in the multimedia content CM for that phase of the set workout program that the user is performing in the set time interval that the multimedia content CM is at.

A displaying mode of this indication is described above.

In an embodiment, in combination with the preceding ones in which reference is made to the at least one first operating parameter P1, in this operating configuration, the step of dynamically modifying 63, after the selection by the user of a value of the at least one first operating parameter P1 (which may also be different from that possibly suggested by the personal trainer in the multimedia content CM), comprises a step of setting 70, by the data processing unit 101, the exercise machine 100 as a function of the value of the at least one first operating parameter P1 selected by the user.

In an embodiment, in combination with the preceding one, the step of dynamically modifying 63, once the user has selected the value of the at least one first operating parameter P1, comprises a step of indicating 71 which value has been selected by the user by the data processing unit 101, e.g., by representing its background in a different color.

In an embodiment, in combination with any of the preceding ones in which the user has selected a value of the at least one first operating parameter P1 and in which an indication is provided on the display module 104 of which among the temporary controls CV-P1 representative of values selectable by the user of at least one first operating parameter P1 of the exercise machine 100 is suggested by the personal trainer in the multimedia content CM, the step of dynamically modifying 63, based on the configuration instructions IC being read together with the playing of the multimedia content CM, if the value of the at least one first operating parameter P1 that the user has selected is different from the suggested value, comprises a step of maintaining 72, by the data processing unit 101, on the display module 104 the indication of which among the temporary controls CV-P1 representative of values selectable by the user of at least one first operating parameter P1 of the exercise machine 100 is suggested by the personal trainer in the multimedia content CM for that phase of the set workout program.

In an embodiment, in combination with any of the preceding ones related to the at least one first operating parameter P1, the step of dynamically modifying 63 is performed, by the data processing unit 101, based on the configuration instructions IC of the exercise machine 100 read together with the playing of the multimedia content CM, to modify the control interface 103 so that it assumes a respective operating configuration to display on the display module 104 temporary controls CV-P2 representative of values selectable by the user of a second operating parameter P2 of the exercise machine 100.

The temporary controls CV-P2 representative of values selectable by the user of a second operating parameter P2 of the exercise machine 100 and their display modes have been described above.

In an embodiment, in combination with the preceding one, the step of dynamically modifying 63 further comprises a step of indicating 73 on the display module 104, by the data processing unit 101, based on the configuration instructions IC of the exercise machine 100 read together with the playing of the multimedia content CM, which of the temporary controls CV-P2 representative of values selectable by the user of a second operating parameter P2 of the exercise machine 100 is suggested by the personal trainer in the multimedia content CM for the phase of the set workout program that the user is performing in the set time interval that the multimedia content CM is at.

A displaying mode of this indication is described above.

In an embodiment in combination with the preceding ones in which reference is made to the second operating parameter P2, in this operating configuration, the step of dynamically modifying 63, after the selection by the user of a value of the at least one first operating parameter P1 (which may also be different from that possibly suggested by the personal trainer in the multimedia content CM), comprises a step of setting 74, by the data processing unit 101, the exercise machine 100 as a function of the value of the second operating parameter P2 selected by the user.

In an embodiment, in combination with the preceding one, the step of dynamically modifying 63, once the user has selected the value of the second operating parameter P2, comprises a step of indicating 75, by the data processing unit 101, which value has been selected by the user, e.g., by representing its background in a different color.

In an embodiment, in combination with any of the preceding ones in which the user has selected a value of the second operating parameter P2 and in which an indication is provided on the display module 104 of which of the temporary controls CV-P2 representative of values selectable by the user of a second parameter P2 of the exercise machine 100 is suggested by the personal trainer in the multimedia content CM, the step of dynamically modifying 63, based on the configuration instructions IC being read together with the playing of the multimedia content CM, if the value of the at least one first operating parameter P1 that the user has selected is different from the suggested value, comprises a step of maintaining 76, by the data processing unit 101, on the display module 104 the indication of which among the temporary controls CV-P2 representative of values selectable by the user of a second operating parameter P2 of the exercise machine 100 is suggested by the personal trainer in the multimedia content CM for that phase of the set workout program.

In an embodiment, in combination with the preceding ones in which reference is made to the at least one first parameter P1, at the end of the time interval corresponding to this operating configuration, in which the user can select a value of the at least one first operating parameter P1, the step of dynamically modifying 63 comprises a step of maintaining 77, by the data processing unit 101, if the user has not made any selection, as a value of the at least one first operating parameter P1 the one previously manually set by the user.

In an embodiment, in combination with the preceding ones in which reference is made to the at least one first parameter P1 and alternatively to the preceding one, at the end of the time interval corresponding to this operating configuration, in which the user can select a value of the at least one first operating parameter P1, the step of dynamically modifying 63 comprises a step of automatically setting 78, by the data processing unit 101, if the user has not made any selection, the value of the at least one first operating parameter P1 suggested by the personal trainer.

Furthermore, in a further embodiment, in combination with any of the preceding ones in which reference is made to the second parameter P2, at the end of the time interval corresponding to this operating configuration, in which the user can select a value a second operating parameter P2, the step of dynamically modifying 63 comprises a step of maintaining 79, by the data processing unit 101, if the user has not made any selection, the value previously set manually by the user as a value of second operating parameter P2.

In an embodiment, in combination with the preceding ones in which reference is made to the second operating parameter P2 and alternatively to the preceding one, at the end of the time interval corresponding to this operating configuration, in which the user can select a value of the second operating parameter P2, the step of dynamically modifying 63 comprises a step of automatically setting 80, by the data processing unit 101, if the user has not made any selection, the second operating parameter P2 suggested by the personal trainer.

In an embodiment, in combination with any of the preceding ones relative to the at least one first operating parameter P1, the step of dynamically modifying 63 comprises a step of shifting 81, by the data processing unit 101, once the value of at least one first operating parameter P1 has been set, the temporary controls CV-P1 representative of values selectable by the user of at least one first operating parameter P1 towards the outside of the display module 104 so that they are partially visible.

According to further embodiments, in combination with the preceding one, the step of shifting 81, by the data processing unit 101, once the value of at least one first operating parameter P1 has been set, the temporary controls CV-P1 representative of values selectable by the user of at least one first operating parameter P1 towards the outside of the display module 104 so that they are partially visible is performed by indicating the set value and/or leaving the respective temporary controls enabled to the pressure.

In an embodiment, in combination with any one preceding one related to the second operating parameter P2, the step of dynamically modifying 63 comprises a step of shifting 82, by the data processing unit 101, once the value of the second operating parameter P2 has been set, the temporary controls CV-P2 representative of values selectable by the user of a second operating parameter P2 towards the outside of the display module 104 at the same time as the temporary controls CV-P1 representative of values selectable by the user of at least one first operating parameter P1 so that they are partially visible, leaving the respective temporary controls enabled to the pressure.

According to further embodiments, in combination with the preceding one, the step of shifting 82, by the data processing unit 101, once the value of the second operating parameter P2 has been set, the temporary controls CV-P2 representative of values selectable by the user of a second operating parameter P2, towards the outside of the display module 104 at the same time as the temporary controls CV-P1 representative of values selectable by the user of at least one first operating parameter P1 so that they are partially visible, is executed indicating the set values and/or leaving the respective temporary controls enabled to the pressure.

According to an embodiment, in combination with any of the preceding ones related to the at least one first operating parameter P1, the step of dynamically modifying 63 further comprises a step of laterally shifting 83, by the data processing unit 101, the temporary controls CV-P1 representative of values selectable by the user of at least one first operating parameter P1 towards the inside of the display module 104 enabling them to be pressed, in response to a touch (tap) made by the user anywhere on the display module 104.

According to an embodiment, in combination with any of the preceding ones related to the second operating parameter P2, the step of dynamically modifying 63 further comprises a step of laterally shifting 84, by the data processing unit 101, temporary controls CV-P2 representative of values selectable by the user of a second operating parameter P2 towards the inside of the display module 104 at the same time as temporary controls CV-P1 representative of values selectable by the user of at least one first operating parameter P1, with the indication of which values were selected by the user enabling them to be pressed in response to a touch (tap) made by the user anywhere on the display module 104.

In an embodiment, either alternative or in combination with any of the preceding ones, the step of dynamically modifying 63 is performed, by the data processing unit 101, based on the configuration instructions IC of the exercise machine 100 read together with the playing of the multimedia content CM, to modify the control interface 103 before (e.g., 5 seconds before) the beginning of a phase of the set workout program so that it assumes a further operating configuration to display temporary controls CV-P1 representative of values selectable by the user of at least one first operating parameter P1 of the exercise machine 100 on the display module 104.

In an embodiment, in combination with the preceding one, the step of dynamically modifying 63 comprises a step of indicating 85 on the display module 104, by the data processing unit 101, based on the configuration instructions IC of the exercise machine 100 read together with the playing of the multimedia content CM, which of the temporary controls CV-P1 representative of values selectable by the user of at least one first operating parameter P1 of the exercise machine 100 is suggested by the personal trainer in the multimedia content CM for that phase of the set workout program that the user is about to perform in the set time interval that the multimedia content CM is about to enter.

In an embodiment, in combination with the preceding one, the step of dynamically modifying 63 is performed, by the data processing unit 101, based on the configuration instructions IC read together with the playing of the multimedia content CM, to modify the control interface 103 before (e.g., 5 seconds before) the beginning of one of the one or more set workout phases so that it assumes a further operating configuration to display temporary controls CV-P2 representative of values selectable by the user of a second operating parameter P2 of the exercise machine 100 on the display module 104 (e.g., the slope of a treadmill).

In an embodiment, in combination with the preceding one, the step of dynamically modifying 63 comprises a step of indicating 86 on the display module 104, by the data processing unit 101, based on the configuration instructions IC read together with the playing of the multimedia content CM, which of the temporary controls CV-P2 representative of values selectable by the user of a second operating parameter P2 of the exercise machine 100 is suggested by the personal trainer in the multimedia content CM for that phase of the set workout program that the user is about to perform in the set time interval that the multimedia content CM is about to enter.

In an embodiment, in combination with any one described above, the step of dynamically modifying 63 comprises a step of displaying 87 on the display module 104, by the data processing unit 101, a first indicator IN1 of the fact that the exercise machine 100 is adjusting (setting) the value of at least one first operating parameter P1 to the value selected by the user.

In an embodiment, in combination with the preceding one, the step of dynamically modifying 63 comprises a step of displaying 88 on the display module 104, by the data processing unit 101, a second indicator IN2 of the fact that the exercise machine 100 is adjusting (setting) the value of the second operating parameter P2 to the value selected by the user.

Other steps of the method related to this further operating configuration (shown in FIG. 5*d*) are the same as other steps previously described with reference to the configuration described in FIG. 5*b* and so they are not repeated here for the sake of brevity.

It is worth noting that the steps of the method described above relating to temporary controls CV-P1 representative of values selectable by the user of the at least one first operating parameter P1 of the exercise machine 100 are implementable in an exercise machine 100, such as a treadmill (P1=speed of the treadmill) or a bike (P1=resistance of the bike).

The steps of the method described above relating to temporary controls CV-P2 representative of values selectable by the user of a second operating parameter P2 of the exercise machine 100 are implementable in an exercise machine 100, such as a treadmill (P2=slope of the treadmill).

In an embodiment, in combination with any one of those described above, if the exercise machine 100 is a bike, the step of dynamically modifying 63 comprises a step of displaying 89 on the display module 104, by the data processing unit 101, a further indicator IN3 of a reference pace value CD to be maintained during the workout.

The method 40 ends with a symbolic step of ending ED.

An example of implementation by an exercise machine 100 of a method for controlling a control interface of an exercise machine during the enjoy of a multimedia content is now described with reference to an embodiment and the aforesaid figures.

A user gets on an exercise machine 100, e.g., a treadmill, to perform physical activity at home.

The user can choose from a plurality of available workouts, e.g., on-demand based on a monthly subscription, or can choose to purchase a single workout from their favorite personal trainer at the time they want to work out.

Once authenticated on the exercise machine 100, the data processing unit 101 of the exercise machine 100 loads the set workout program of the user to be performed and plays the multimedia content CM of the personal trainer preparatory to performing the set workout program.

After the beginning of the playing of the multimedia content CM (e.g., a few seconds after), based on the configuration instructions IC read together with the playing of the multimedia content CM, the data processing unit 101 modifies the control interface 103 so that it assumes a respective operating configuration in which to display on the display module 104 temporary controls CV-L representative of the initial workout difficulty levels selectable by the user (FIG. 5a).

The personal trainer in the multimedia content CM tells the user to select the initial workout difficulty level.

The user selects an initial workout difficulty level (e.g., intermediate).

Once the initial workout difficulty level is set, the data processing unit 101 removes from the display module 104 temporary controls CV-L representative of workout levels selectable by the user.

It is worth noting that the user always has a control LD available to vary the workout difficulty level at any time during the workout.

After setting the initial workout difficulty level, the data processing unit 101, based on the configuration instructions IC read together with the playing of the multimedia content CM, modifies the control interface 103 so that it assumes a respective operating configuration to display on the display module 104 temporary controls CV-P1 representative of values selectable by the user of at least a first operating parameter P1 of the exercise machine 100 (e.g., speed of the treadmill) and temporary controls CV-P2 representative of values selectable by the user of a second operating parameter P2 of the exercise machine 100 (e.g., slope of the treadmill).

The temporary controls CV-P1 representative of values selectable by the user of at least one first operating parameter P1 and of the temporary controls CV-P2 representative of values selectable by the user of a second operating parameter P2 are displayed, by the data processing unit 101, by making such controls enter from one side of the display module 104 and making them scroll horizontally to their definitive position (e.g., the right side and on the left side of the display module 104, as shown in FIG. 5b).

Furthermore, the data processing unit 101, based on the configuration instructions IC read together with the playing of the multimedia content CM indicates on the display module 104 (using one or more arrows F1 and F2) which of the temporary controls CV-P1 representing values selectable by the user of at least one first operating parameter P1 and which of the temporary controls CV-P2 representative of values selectable by the user of a second operating parameter P2 of the exercise machine 100 is suggested by the personal trainer in the multimedia content CM for that phase of the set workout program that the user is performing in the set time interval that the multimedia content CM is at.

The multimedia content CM of the personal trainer tells the user to select a value for the first operating parameter P1 and a value for the second operating parameter P2.

The user promptly selects the suggested values (clearly indicated by the F1 and F2 arrows) of both the first operating parameter P1 and the second operating parameter P2.

The data processing unit 101 sets the exercise machine 100 based on the temporary controls CV made available by the control interface 103 and selected by the user through the control interface 103 in said operating configuration.

In greater detail, the data processing unit 101 sends respective control signals representative of temporary controls CV selected by the user to one or more components of the exercise machine 100.

For example, the data processing unit 101 sends a respective control signal to a motor of the treadmill to set the speed at the selected value and a respective control signal to a actuator of the treadmill which will implement the selected slope value.

At this point, the data processing unit 101 shifts the temporary controls CV-P1 representative of the values selectable by the user of the at least one first operating parameter P1 and the temporary controls CV-P1 representative of the values selectable by the user of the second operating parameter P2 towards the outside of the display module 104 so that they are partially visible, indicating the set values, i.e., those selected by the user (FIG. 5c).

In this manner, the user can see the multimedia content CM in its entirety, without the risk of inadvertently changing the previously set operating parameters of the exercise machine.

In response to a very easily executed touch (tap) by the user anywhere on the display module 104, the data processing unit 101 laterally shifts towards the inside of the display module 104 both temporary controls CV-P1 representative of values selectable by the user of the at least one first operating parameter P1 and temporary controls CV-P2 representative of values selectable by the user of a second operating parameter P2 (with an indication of which values were previously selected by the user).

The user promptly selects other values of the first operating parameter P1 and the second operating parameter P2.

The multimedia content CM and the set workout program end.

It is worth noting that the scope of the invention is fully achieved.

Indeed, the method according to the present invention allows the control interface 103 of the exercise machine 100 to assume operating configurations in which temporary CV controls are displayed on the display module 104 of the control interface 103, which closely follow the reproduced multimedia content CM, thus enabling only temporary portions of the display module 104 of the control interface 103 (of touchscreen type) to be pressed by the user, reducing the possibility of error and allowing the user to follow at the best the set workout program to which the multimedia content refers.

Furthermore, the manner in which temporary controls CV are displayed and the indication of the suggestions provided by the personal trainer in the multimedia content CM allow the user to identify these controls promptly and intuitively and follow the progress of the set workout program, even under stress and/or in the presence of background noise in the workout class or the gym.

Other described operating configurations allow the user a simple and intuitive interaction with the control interface 103, such as a simple touch (tap) allows the user to reset an operating configuration in which to select different operating parameters of the exercise machine during the workout.

Those skilled in the art may make changes and adaptations to the embodiments of the method and the exercise machine described above or can replace elements with others which are functionally equivalent to meet contingent needs without departing from the scope of protection as described and claimed herein. All the features described above as belonging to a possible embodiment may be implemented independently of the other described embodiments.

What is claimed is:

1. A method for controlling a control interface of an exercise machine during the consumption of multimedia content, the method comprising:
   providing multimedia content of a personal trainer preparatory to a performance of a set workout program on the exercise machine, configured to be consumed by a user through the control interface of the exercise machine;
   associating configuration instructions of the exercise machine with the multimedia content, which can be read by a data processing unit of the exercise machine, synchronized with playing of the multimedia content;
   a step of dynamically modifying, via the data processing unit, wherein if an instant of playing time falls within a set time interval provided by the configuration instructions, the control interface is dynamically modified so that it takes a first operating configuration corresponding to a set time interval reached by the multimedia content;
   in said first operating configuration, simultaneously showing the user, by the data processing unit, on one lateral side of a display module of the control interface, a first plurality of temporary controls made available by the control interface and enabled to be used by the user through the control interface; and
   physically setting, by the data processing unit, the exercise machine based on the first plurality of temporary controls made available by the control interface and selected by the user through the control interface in said first operating configuration;
   wherein the step of dynamically modifying is performed, by the data processing unit, based on the configuration instructions of the exercise machine read together with the playing of the multimedia content, to modify the control interface so that it assumes a second operating configuration to simultaneously display on the display module a plurality of temporary controls representative of values selectable by the user of at least one first operating parameter of the exercise machine, each of the temporary controls showing the corresponding value;
   wherein the step of dynamically modifying further comprises a step of indicating, by the data processing unit, based on the configuration instructions of the exercise machine read together with the playing of the multimedia content, wherein it is indicated on the display module which of the first plurality of temporary controls representative of values selectable by the user of the at least one first operating parameter of the exercise machine is suggested by the personal trainer in the multimedia content for a phase of the set workout program that the user is performing in the set time interval that the multimedia content is at;
   wherein the step of dynamically modifying, based on the configuration instructions read together with the playing of the multimedia content, further comprises recognizing that the value of the at least one first operating parameter that the user has selected is different from the suggested value, and in response to said recognizing, maintaining, by the data processing unit, on said one lateral side of the display module the indication of which of the temporary controls representative of values selectable by the user of at least one first operating parameter of the exercise machine is suggested by the personal trainer in the multimedia content for that phase of the set workout program; wherein the step of dynamically modifying further comprises a step of automatically setting, at an end of a time interval corresponding to the third operating configuration, via the data processing unit, wherein if the user has not made any selection, a first initial workout difficulty level will be set automatically and a step of automatically setting, at an end of a time interval corresponding to the third operating configuration, via the data processing unit, wherein if the user has not made any selection, a first initial workout difficulty level will be set automatically;
   wherein said exercise machine is a treadmill, a bike or exercise bike, a rowing machine, an indoor cycling machine, a strength exercise machine, or a station for practicing boxing.

2. The method of claim 1, wherein the step of dynamically modifying is performed, by the data processing unit, based on the configuration instructions of the exercise machine read together with the playing of the multimedia content to dynamically modify the control interface so that it takes a third operating configuration to display on the display module temporary controls representative of values selectable by the user of a second operating parameter of the exercise machine.

3. The method of claim 2, wherein the step of dynamically modifying comprises a step of shifting, by the data processing unit, once the value of the second operating parameter has been selected, wherein the temporary controls representative of values selectable by the user of the second operating parameter are shifted towards an outside of the display module at a same time as the temporary controls representative of values selectable by the user of the at least one first operating parameter so that they are partially visible.

4. The method of claim 3, wherein the step of shifting, by the data processing unit, once the value of the second operating parameter has been selected, wherein the temporary controls representative of values selectable by the user of the second operating parameter are shifted towards the outside of the display module at the same time as the temporary controls representative of values selectable by the user of at least one first operating parameter are shifted so that they are partially visible is executed indicating the set values and/or leaving the respective temporary controls enabled to pressure.

5. The method of claim 3, wherein the step of dynamically modifying further comprises a step of laterally shifting, by the data processing unit, wherein the temporary controls representative of values selectable by the user of the second operating parameter are laterally shifted towards the inside of the display module at the same time as the temporary controls representative of values selectable by the user of the at least one first operating parameter, enabling them to be pressed in response to a touch made by the user anywhere on the display module.

6. The method of claim 2, wherein the step of dynamically modifying further comprises a step of indicating, by the data processing unit, based on the configuration instructions read together with the playing of the multimedia content, wherein it is indicated on the display module which of the temporary controls representative of values selectable by the user of the second operating parameter of the exercise machine is suggested by the personal trainer in the multimedia content for the phase of the set workout program that the user is performing in the set time interval that the multimedia content is at.

7. The method of claim 1, wherein the step of dynamically modifying comprises a step of shifting, by the data processing unit, once the value of the at least one first operating parameter has been set, wherein the temporary controls representative of values selectable by the user of the at least one first operating parameter are shifted towards an outside of the display module so that they are partially visible.

8. The method of claim 7, wherein the step of dynamically modifying further comprises a step of laterally shifting, by the data processing unit, wherein the temporary controls representative of values selectable by the user of the at least one first operating parameter are laterally shifted towards an inside of the display module enabling them to be pressed, in response to a touch made by the user anywhere on the display module.

9. The method of claim 1, comprising, at starting playing the multimedia content, a step of dynamically modifying, by the data processing unit, based on the configuration instructions of the exercise machine read together with the playing of the multimedia content, the control interface so that it assumes a third operating configuration to display fixed controls of a plurality of controls made available to the user on the display module of the control interface.

10. The method of claim 1, wherein the step of dynamically modifying comprises a step of removing, via the data processing unit, once the initial workout difficulty level has been selected, wherein the temporary controls representative of the initial workout difficulty levels selectable by the user on the display module are removed.

11. The method of claim 1, wherein, at an end of the time interval corresponding to the second operating configuration, the step of dynamically modifying comprises a step of setting the exercise machine, by the data processing unit, wherein the exercise machine is set as a function of the value of said at least one first operating parameter selected by the user.

12. The method of claim 1, wherein the values selectable by the user of the at least one first operating parameter of the exercise machine are a function of an initial workout difficulty level selected by the user.

13. The method of claim 1, wherein which of the temporary controls representative of values selectable by the user of the at least one first operating parameter of the exercise machine is suggested is a function of an initial workout difficulty level selected by the user.

14. The method of claim 1, wherein after an interval in which the user can select one of said values, if a value has not been selected, the value of the at least one first operating parameter suggested by the personal trainer is automatically selected.

15. The method of claim 1, wherein it is indicated by one or more arrows on the display module which of the temporary controls representative of values selectable by the user of the at least one first operating parameter of the exercise machine is suggested by the personal trainer in the multimedia content for a phase of the set workout program that the user is performing in the set time interval that the multimedia content is at.

16. An exercise machine comprising:
a data processing unit;
a control interface, operationally connected to the data processing unit, comprising a display module;
the data processing unit being configured to perform:

providing multimedia content of a personal trainer preparatory to a performance of a set workout program on the exercise machine, configured to be consumed by a user through the control interface of the exercise machine;

associating configuration instructions of the exercise machine with the multimedia content, which can be read by a data processing unit of the exercise machine, synchronized with playing of the multimedia content;

a step of dynamically modifying, via the data processing unit, wherein if an instant of playing time falls within a set time interval provided by the configuration instructions, the control interface is dynamically modified so that it takes a first operating configuration corresponding to a set time interval reached by the multimedia content;

in said first operating configuration, simultaneously showing the user, by the data processing unit, on one lateral side of a display module of the control interface, a first plurality of temporary controls made available by the control interface and enabled to be used by the user through the control interface; and physically setting, by the data processing unit, the exercise machine based on the first plurality of temporary controls made available by the control interface and selected by the user through the control interface in said first operating configuration;

wherein the step of dynamically modifying is performed, by the data processing unit, based on the configuration instructions of the exercise machine read together with the playing of the multimedia content, to modify the control interface so that it assumes a second operating configuration to simultaneously display on the display module a plurality of temporary controls representative of values selectable by the user of at least one first operating parameter of the exercise machine, each of the temporary controls showing the corresponding value; and wherein the step of dynamically modifying further comprises a step of indicating, by the data processing unit, based on the configuration instructions of the exercise machine read together with the playing of the multimedia content, wherein it is indicated on the display module which of the first plurality of temporary controls representative of values selectable by the user of the at least one first operating parameter of the exercise machine is suggested by the personal trainer in the multimedia content for a phase of the set workout program that the user is performing in the set time interval that the multimedia content is at;

wherein the step of dynamically modifying, based on the configuration instructions read together with the playing of the multimedia content, further comprises recognizing that the value of the at least one first operating parameter that the user has selected is different from the suggested value, and in response to said recognizing, maintaining, by the data processing unit, on said one lateral side of the display module the indication of which of the temporary controls representative of values selectable by the user of at least one first operating parameter of the exercise machine is suggested by the personal trainer in the multimedia content for that phase of the set workout program; wherein the step of dynamically modifying further comprises a step of automatically setting, at an end of a time interval corresponding to the third operating configuration, via the data processing unit, wherein if the user has not made any selection, a first initial workout difficulty level will be set automatically and a step of automatically setting, at an end of a time interval corresponding to the third operating configuration, via the data processing unit, wherein if the user has not made any selection, a first initial workout difficulty level will be set automatically;

wherein said exercise machine is a treadmill, a bike or exercise bike, a rowing machine, an indoor cycling machine, a strength exercise machine, or a station for practicing boxing.

17. The exercise machine of claim 16, wherein said at least one first operating parameter comprises:
speed and/or slope of said treadmill;
resistance of said bike or exercise bike;
resistance of said rowing machine;
resistance of said indoor cycling machine; or
resistance of said strength exercise machine.

\* \* \* \* \*